United States Patent
Shimko et al.

(10) Patent No.: US 9,737,071 B2
(45) Date of Patent: *Aug. 22, 2017

(54) COMPOSITIONS AND METHODS FOR ENHANCING THE VIABILITY OF ANIMAL CELLS, TISSUES, AND ORGAN EXPLANTS

(71) Applicant: Warsaw Orthopedic, Inc., Warsaw, IN (US)

(72) Inventors: Daniel Andrew Shimko, Germantown, TN (US); Scott P. Noel, Arlington, TN (US); Susan J. Drapeau, Cordova, TN (US); Josee Roy, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/582,837

(22) Filed: Dec. 24, 2014

(65) Prior Publication Data

US 2015/0140543 A1    May 21, 2015

Related U.S. Application Data

(60) Continuation of application No. 12/950,368, filed on Nov. 19, 2010, now Pat. No. 8,927,202, which is a division of application No. 11/777,167, filed on Jul. 12, 2007, now Pat. No. 7,892,724.

(51) Int. Cl.
*A01N 1/02* (2006.01)
*C12N 5/00* (2006.01)

(52) U.S. Cl.
CPC ............ *A01N 1/0226* (2013.01); *A01N 1/02* (2013.01); *A01N 1/021* (2013.01); *C12N 5/0018* (2013.01); *C12N 2500/30* (2013.01); *C12N 2500/46* (2013.01); *C12N 2500/60* (2013.01)

(58) Field of Classification Search
None
See application file for complete search history.

(56) References Cited

U.S. PATENT DOCUMENTS

| | | |
|---|---|---|
| 4,798,824 A | 1/1989 | Belzer et al. |
| 4,927,762 A | 5/1990 | Darfler |
| 5,110,721 A | 5/1992 | Anaise et al. |
| 5,110,722 A | 5/1992 | Brockbank et al. |
| 5,118,512 A | 6/1992 | O'Leary et al. |
| 5,145,771 A | 9/1992 | Lemasters et al. |
| 5,200,398 A | 4/1993 | Strasberg et al. |
| 5,217,860 A | 6/1993 | Fahy et al. |
| 5,230,996 A | 7/1993 | Rath et al. |
| 5,336,616 A | 8/1994 | Livesey et al. |
| 5,552,267 A | 9/1996 | Stern et al. |
| 5,693,462 A | 12/1997 | Raymond |
| 5,719,174 A | 2/1998 | Sainsbury et al. |
| 6,355,409 B1 | 3/2002 | Boelsterli |
| 6,495,532 B1 | 12/2002 | Bathurst et al. |
| 6,696,238 B2 | 2/2004 | Murphy et al. |
| 6,994,954 B2 | 2/2006 | Taylor |
| 7,129,035 B2 | 10/2006 | Goldstein et al. |
| 2005/0156378 A1 | 7/2005 | Steinhardt |
| 2008/0293034 A1 | 11/2008 | Dobson |
| 2009/0017438 A1 | 1/2009 | Roy et al. |

OTHER PUBLICATIONS

Potts et al., "Traumatic Injury to the Immature Brain: Inflammation, Oxidative Injury, and Iron-Mediated Damage as Potential Therapeutic Targets", Journal of the American Society for Experimental NeuroTherapeutics 2006, vol. 3, pp. 143-153.*
Dansa-Petretski, M., et al., "Antioxidant Role of Rhodnius prolixus Herne-binding Protein," The Journal of Biological Chemistry, vol. 270, No. 18, Issue of May 5, pp. 10893-10896(1995).
Zhan, Y., Antioxidant Activities of Aqueous Extract from Cultivated Fruit-Bodies of *Cordyceps militaris* (L) Link In Vitro, Journal of Integrative Plant Biology, vol. 48, No. 11, pp. 1365-1370 (2006).
Toledo-Pereyra, M.D., et al., "Factors Determining Successful Liver Preservation for Transplantation", From the Department of Surgery, University of Minnesota Hospitals, Minneapolis, MN, Sep. 3, 1974, vol. 181—No. 3, 289-298.
Baust, et al., "Cryopreservation, an emerging paradigm change", Organogenesis 5:3, 90-96; Jul./Aug./Sep. 2009; © 2009 Landes Bioscience, vol. 5, Issue 3.
Brenner, "The Genetics of Caenorhabditis elegans", Medical Research Council Laboratory of Molecular Biology, Hills Road, Cambridge, CB2 2QH, England, Manuscript received Dec. 10, 1973, Genetics 77 : 71-94 May 1974.
Mouzas, M.D., "The present status of organ preservation: a review", Current Survey, Department of Surgery, Yale University, New Haven, Connecticut, Postgrad. med. J. {Nov. 1967) 43, 712-715.
Sosef, M.D., et al., Cryopreservation of Isolated Primary Rate Hepatocytes, Enhanced Survival and Long-term Hepatospecific Function, Annals of Surgery, vol. 241, No. 1, Jan. 2005, pp. 125-133.
Randell, et al., Uptake of Non-Transferrin-bound Iron by Both Reductive and Nonreductive Processes is Modulated by Intracellular Iron, the Journal of Biological Chemistry, 1994, pp. 16046-16053, vol. 269, No. 23, Issue of Jun. 10, the American Society for Biochemistry and Molecular Biology, Inc., U.S.A.

(Continued)

*Primary Examiner* — Renee Claytor
*Assistant Examiner* — Michelle F Paguio Frising

(57) ABSTRACT

Disclosed are compositions and methods for the preservation, storage, and transport of living biological tissues, organs, and populations of isolated cells. In particular, the disclosed compositions and processes permit mammalian cells, tissues, and organs to be harvested from suitable donor animals, stored for prolonged periods, and transported to the site of recipient implantation, all without significant loss of cell viability, biological activity, and/or tissue integrity.

15 Claims, 9 Drawing Sheets

(56) References Cited

OTHER PUBLICATIONS

Figure 1:
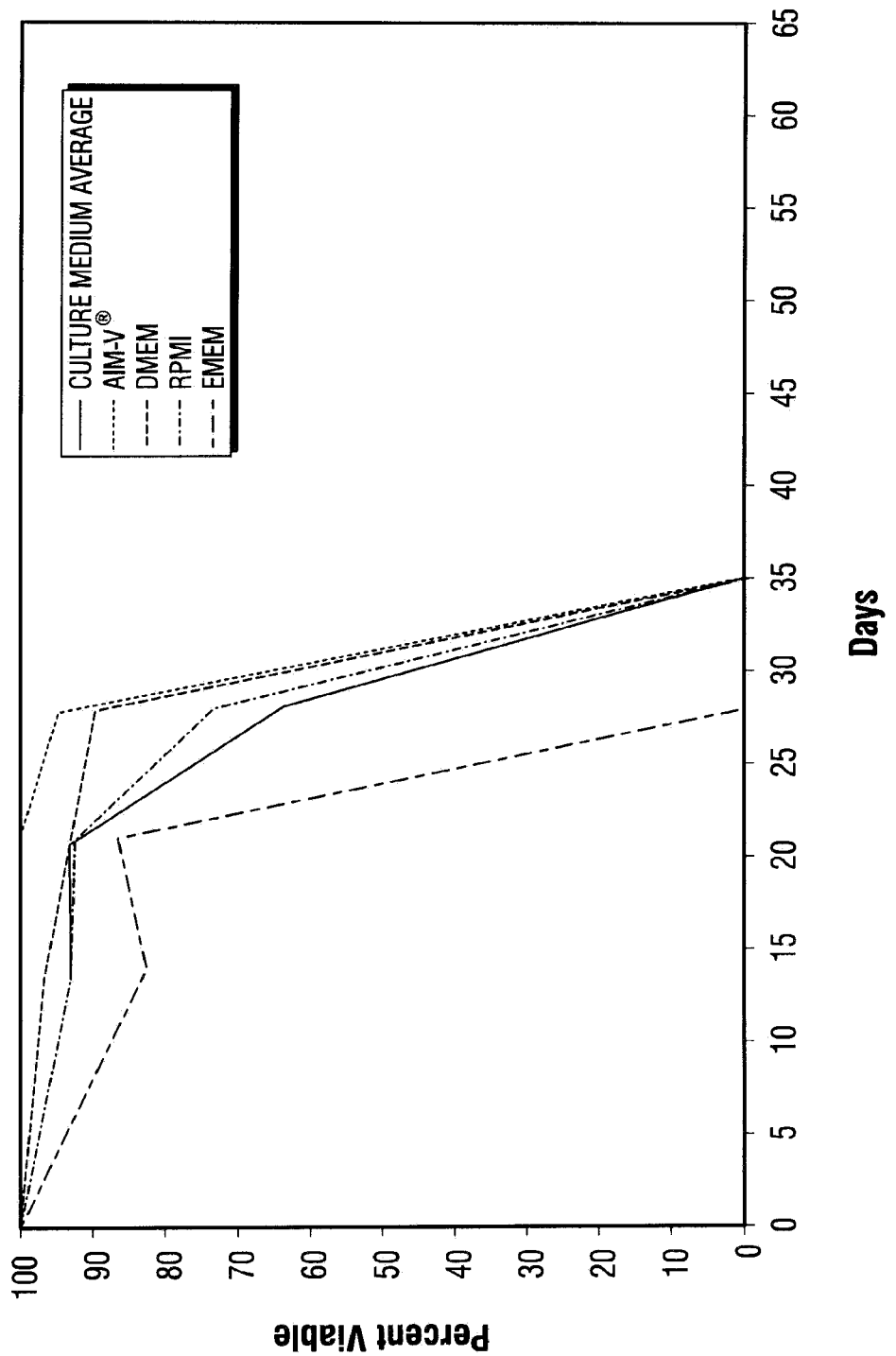

Yang, et al., Effect of Cardioplegic and Organ Preservation Solutions and Their Components on Coronary Endothelium-Derived Relaxing Factors, the Annals of Thoracic Surgery, 2005, the Society of Thoracic Surgeons, http://ats.ctsnetjournals.org/cgi/content/abstract/80/2/757.

Cragg, et al., The Iron Chelator L1 Potentiates Oxidative DNA Damage in Iron-Loaded Liver Cells, Blood, 1998, pp. 632-638, vol. 92, No. 2, the American Society of Hematology.

Michael, et al., Oxidant Stress Regulates Basal Endothelin-1 Production by Cultured Rat Pulmonary Endothelial Cells, 1997, pp. L768-L774, Am. J. Physiol. 273 (Lung Cell. Mol. Physiol. 17).

Aoshiba, et al., Thiol Depletion Induces Apoptosis in Cultured Lung Fibroblasts, Am. J. Respir. Cell Mol. Biol., 1999, pp. 54-63, vol. 21, www.atsjournals.org.

\* cited by examiner

COMPOSITIONS AND METHODS FOR ENHANCING THE VIABILITY OF ANIMAL CELLS, TISSUES, AND ORGAN EXPLANTS

This application is a continuation application of U.S. patent application Ser. No. 12/950,368 filed Nov. 19, 2010, entitled "COMPOSITIONS AND METHODS FOR ENHANCING THE VIABILITY OF ANIMAL CELLS, TISSUES, AND ORGAN EXPLANTS," which is a divisional of U.S. patent application Ser. No. 11/777,167 filed Jul. 12, 2007, now U.S. Pat. No. 7,892,724 entitled "COMPOSITIONS AND METHODS FOR ENHANCING THE VIABILITY OF ANIMAL CELLS, TISSUES AND ORGAN EXPLANTS." These entire disclosures are incorporated herein by reference into the present disclosure.

1. FIELD OF THE INVENTION

The present application relates generally to the field of biological tissue preservation, storage, and transport. In particular, compositions and methods are provided to extend the post-harvest viability and enhance the preservation, storage and/or transport of a wide variety of biological samples, including e.g., mammalian cells, tissues, organs, and tissue engineered products. Also provided are methods and processes for enhancing cellular viability, maintaining tissue integrity, and prolonging the suitability of a variety of mammalian cells, tissues, and organ explants.

2. BACKGROUND

Almost one million tissue allografts are transplanted each year in the United States. Approximately 700,000 bone grafts are done yearly, although it is estimated that another 300,000 patients could be helped if there were enough viable allograft bone tissue available. Transplanted skin is grafted in more than one million procedures worldwide each year, with three-quarters of this usage occurring in life-saving circumstances such as severe burns. Another 500,000 burn patients, however, could have their wound-healing time shortened if enough viable allograft skin was available from tissue banks. Similarly, corneal replacements are performed on nearly 50,000 patients each year to restore sight—another 20,000 patients, however, are turned away due to a lack of viable corneas.

A significant limitation to meeting the annual worldwide need for more tissue allografts and organs is the relative difficulty for controlling the delicate balance between the "supply" of viable explants from suitable donors and the "demand" of transplant candidates across the globe. Even in those circumstances in which suitable donor(s) and recipient(s) can be matched, another important limitation is the ability to store, screen, match, and transport tissues along the path from the site of donor harvest, to the site of the tissue storage repository, and then onward to the site of recipient transplant—a path that in many instances, may involve many days and many thousands of miles.

Perhaps the most confounding element of the migration of explanted tissues from donor to recipient is the relatively short period, post-harvest, in which the tissue or organ remains both viable, and suitable for transplantation. Unlike mammalian blood and blood components, which may be harvested and "banked" for several weeks without significant loss of viability, most explained mammalian tissues and organs in contrast, are quite fragile. For example, the post-harvest time interval during which many human tissues remain viable (even if stored and transported under currently ideal conditions) is typically only a few days. Similarly, most mammalian organs rapidly lose viability and function after removal from the donor, and may become unsuitable for transplantation after extracorporeal storage and transport as soon as six- to eight-hours post-harvest.

Even for mammalian tissues that are most amenable to post-harvest tissue banking, the critical "window of opportunity" between harvest and transplant is only a few weeks at best. As a result, often there is not enough time to match donors and recipients, test the quality and suitability of the explant, transport the tissue from the donor to the recipient, and implant the tissue into the recipient. Consequently, there are substantially more recipients awaiting transplants than there are suitable donor tissues available for transplant.

The fact that conventional buffer solutions, physiological formulations, diluents, standard culture media, cellular growth media, tissue storage solutions, and organ transport media are typically only able to preserve the cellular viability and suitability of biological tissues or organs for transplantation for a period of a few hours to a few days post-harvest makes them largely unsuitable for prolonged- or extended-term storage of viable biological materials such as mammalian cells, tissues, organs, explants, and such like. In particular, what has been most lacking in the prior art, are compositions and methodologies that facilitate the long-term preservation of cell, tissue, and organ viability, and that maintain the biological activity, function and tissue integrity.

Moreover, what is also lacking is the ability to store such biological samples for extended periods of time, and still maintain suitability of the extended-storage product for transplanting into recipient animals, particularly when the period of time from initial harvest to ultimate transplantation in a recipient host is on the order of several weeks' to several months' duration.

3. SUMMARY

The present invention overcomes these and other limitations inherent in prior methodologies by providing methods and compositions that permit harvest, maintenance, storage, and/or transport of a variety of biological materials including, for example, mammalian cells, tissues, and organs for periods extending from several hours to several days or weeks—even up to and including several months post-harvest. Using the methods and compositions disclosed herein, the inventors have successfully demonstrated the retention of significant cellular viability in harvested biological cells, tissues, explants, organs, etc. for substantially extended periods, and believe that these compositions and methods offer important new tools for prolonging the biochemical activity, preserving the anatomical function, and/or maintaining the tissue integrity of a variety of post-harvest mammalian cells, tissues, organs, explants, and such like.

In a dramatic improvement over contemporary tissue storage methodologies, the inventors have developed tissue-viability-preserving compositions and methods that facilitate the intermediate- and/or long-term storage of biological samples such as mammalian cells, tissues, and organs, without significant loss in cellular viability or tissue integrity, even when the tissues are stored over periods from several days, to several weeks. Previously recalcitrant and poorly perfusable mammalian tissues such as bone, cartilage, ligaments, tendons, meniscus, intervertebral discs, and such like may now be stored for prolonged periods following harvest (i.e., removal of the cells, tissues, or organs from the body of the donor animal).

The invention also provides those in the medical transplantation arts the ability to create tissue and organ banks by increasing the window of opportunity from donor harvest to recipient implant during which the cells and tissues remain viable and amenable to transplantation in a suitable recipient. The development of these tissue banks may be greatly facilitated using one or more of the pharmaceutically-acceptable tissue viability-enhancing compositions described herein—particularly in the context of maintaining the viability, and preserving the biological function of, one or more mammalian autograft, allograft, isograft, and/or xenograft tissue(s) prior to transplantation.

The inventors have improved upon many of the previously-available cell and tissue storage modalities by providing for the first time storage solutions that permit extended, intermediate- and/or long-term preservation and/or storage of a variety of biological samples or biological materials, including for example, populations of viable cells, mammalian tissues, organs, explants, and such like under conditions that preserve the suitability of such biological material(s) for transplantation into a recipient mammal in need thereof.

The methods described herein allow sufficient time for collecting natural, culture-derived, or recombinantly-engineered populations of mammalian cells, or for harvesting cells, tissues, or organs from a donor animal, testing them for donor/recipient compatibility and/or lack of toxicity/pathogenicity to the recipient host, and then storing and/or transporting them (often for an extended period of time) to the site for transplantation of the cells, tissues, or organs occurs into the body of a suitable animal recipient host. The methods disclosed herein are particularly valuable for increasing the time interval between collection/harvest of mammalian cells, tissues, grafts (and in particular, the poorly-perfusable tissues such as bone, cartilage, and osteocartilagenous, ligamentary, tendinous, and discogenic tissues, etc.), and subsequent implantation into recipient animals, for extending the shelf-life of processed cells or tissues, and for maintaining cellular viability and tissue integrity substantially for periods substantially longer than that afforded by many of the tissue storage/preservation/organ transport solutions routinely in use today in the field of transplantation medicine.

4. DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Conventional biological buffers, cell culture media, biological media, tissue growth media, mammalian tissue, explant, and/or organ storage solutions, or biological transport buffers, preservation media, and such like, permit only relatively short-term storage and/or transport of mammalian cells, tissues, or organs before the cells, tissues, or organs are degraded, lose viability, lack sufficient structural integrity and/or become otherwise unsuitable or unsafe for long-term storage, or for transplantation into a suitable recipient host.

In sharp contrast, however, the compositions and methods disclosed herein provide a dramatic improvement in the skilled artisan's ability to prepare and use one or more such compositions to support long-term viability and suitability of such biological materials for periods of from several weeks to several months or more.

The cellular viability, tissue integrity, and biological function of a variety of mammalian cells or tissues has been prolonged for periods ranging from several days to several weeks, and even to several months by utilizing one or more of the disclosed compositions—without significant loss of biological activity, cellular viability, or tissue implant suitability. Moreover, the processes disclosed herein for the storage and/or transport of such biological samples have been shown to extend significantly the "shelf-life" of harvested donor cells, tissues or organs. Importantly, the present compositions and methods have been shown to facilitate intermediate- and/or long-term storage (i.e., banking) of a variety of biological samples under conditions suitable for maintaining the viability, integrity, or cellular activity of such samples in scenarios that are analogous to contemporary methodologies for the extended storage of viable blood and/or blood components that remain suitable for introduction into a suitable recipient organism.

The present invention provides novel methods and compositions for prolonging the viability, extending the "shelf-life," and maintaining the biological activity and/or tissue integrity of stored populations of animal cells, and in particular, mammalian cells, tissues and/or organs. The methods and compositions provided herein significantly improve upon existing methods of tissue and organ storage, and provide new means for substantially prolonging the cellular viability of explanted biological material post-harvest. These methods dramatically increase the time interval during which explanted biological material remains viable and suitable for transplantation, and thus lengthens the critical window between the initial harvesting of tissues/organs and their subsequent implantation in a suitable recipient.

The inventors have demonstrated, inter alia, that conventional biological storage buffers, cell culture media, growth media, organ storage solutions, and biological transport buffers/diluents, and such like permit only a very short time interval between harvest and implantation in which the cell(s), tissue(s) or organ(s) remains viable, and hence suitable for implantation. The inventors have improved upon these inferior methodologies by developing novel compositions and methods that permit, for the first time, intermediate- and long-term preservation of animal cells, tissues, and organs for periods of time ranging from several days to several weeks, without significant loss of substantial biological activity, cellular viability, or tissue implant suitability even in biological materials that are explanted, prepared, and then stored for several weeks to several months or more, without substantial loss of tissue viability and/or implant suitability.

In a manner analogous to the storage of blood and blood components in "blood banks," the present invention provides for the first time, the ability of the medical arts to create "tissue banks" or "organ banks" to maintain viable mammalian explant(s) for periods of time of from several days to several weeks, instead of conventional limitations which often provide suitable implantable material only if stored for several minutes to hours, following harvest from suitable donor sources, and prior to transplantation into one or more suitable recipient individuals. The development of such tissue/organ banks is greatly facilitated by the development of the novel compositions described herein, and particularly in the context of providing populations of viable cells, one or more tissue(s) or organ(s) including, for example, autograft, allograft, isograft, or xenograft tissues that are destined for transplantation into a suitable mammalian recipient, and into suitable human patients in particular.

While conventional tissue preserving methodologies currently limit the time interval possible from tissue harvest to implantation from a few minutes to a few hours, and in rare instances, for a few days, in illustrative examples provided herein, the inventors have developed a number of novel tissue-viability-preserving compositions and methods to facilitate the intermediate- and/or long-term storage of biological samples or materials (e.g., cultured or harvested cells, tissue explants, organs, and such like) without significant loss in cellular viability, biological functional, tissue integrity, or host-recipient compatibility, etc. for periods of time that extend several days, several weeks, or even several months post-collection or post-harvest.

The present invention provides cell-, tissue-, and organ-preserving solutions for use in the collection, analysis, screening, storage, transport, and transplantation of such harvested biological materials into a recipient animal. These compositions exhibit superior performance, provide enhanced cellular preservation capabilities, and enhance maintenance of cellular viability, when compared to the use of existing preservation solutions, or biological buffers or media alone.

The disclosed compositions and methods are particularly useful in extending the time between collection/harvest of biological material(s) from a donor source to the subsequent transplantation or introduction of such material(s) into at least a first site in the body of a suitable recipient animal, compared to conventional storage and transport regimens. These compositions, and the methods disclosed herein employing them, significantly extend the "shelf-life" of harvested donor cells, tissues and organs. Importantly, these compositions and methods facilitate, for the first time, storage of a biological sample under conditions that maintain the viability, integrity, structure, and/or function of such biological material for a period of at least several weeks to several months' post-collection.

The present invention provides cell-, tissue-, and organ-preserving solutions for use in the collection, analysis, screening, storage, transport, and transplantation of such harvested biological materials into a recipient animal. These compositions exhibit superior performance and provide enhanced cellular preservation capabilities and enhanced maintenance of cellular viability, when compared to the use of existing preservation solutions, physiological fluids, diluents, or biological buffers or cell growth and/or culture media alone.

In a first embodiment, the invention provides a method for storing and/or transporting one or more populations of mammalian cells, tissues, or organs, under conditions that permit long-term retention of viability and/or biological activity and/or function. In an overall and general sense, this method generally comprises at least the steps of (a) contacting a population of mammalian cells, or a mammalian tissue or organ with a composition that comprises, consists essentially of, or consists of: (i) at least one biologically-acceptable medium, diluent, storage buffer, or transport solution; (ii) at least one biomembrane sealing agent; (iii) at least one chelator; and (iv) at least one antioxidant; and (b) maintaining the population of mammalian cells or the mammalian tissue or organ in the composition substantially at a temperature of from between about −10° C. to about 30° C., under conditions wherein the population of mammalian cells or the mammalian tissue or organ remains substantially viable both during storage and immediately thereafter maintaining such cells or tissues/organs in a physiologic state that is suitable for their implantation into a selected recipient mammal.

While it is contemplated that the disclosed formulations will most often be employed for the storage and/or transport of tissues at temperatures in the range of about −10° C. to about 30° C. (with the proviso that at least a portion of the storage solution preferably remains substantially in an unfrozen, thawed, or liquid state), it has been demonstrated that viability of stored animal tissues (and in particular, explanted mammalian tissues) is greatly enhanced by the present invention when the tissue preparations are stored under conditions of standard laboratory refrigeration conditions, such as for example, at a temperature of from about 1° C. or 2° C. up to and including storage at a temperature of from about 5° C. to about 10° C. Maintenance of the tissue sample or organ in the disclosed compositions substantially at a temperature on the order of about 3° C. or 4° C. to about 6° C. or 7° C. (corresponding to average temperature of conventional laboratory refrigerated storage compartments, refrigerator units, and such like). While it is contemplated that slight variation in temperature during the storage/transport process will not adversely affect the integrity, biological function, or cellular viability of the stored tissue or organ, it is preferable that the material be maintained and transported under environmental conditions of approximately 0° C. to about 10° C. whenever possible.

Preferably, by using the compositions described herein, a population of mammalian cells or a selected mammalian tissue or organ may remain substantially viable, and as such, retain substantial biologic activity, while stored in, and/or transported in, such a composition, for periods of time that are significantly longer than those afforded by the many conventional biological buffers, or cell culture media, physiologic solutions, biological storage solutions, and/or organ transport solutions found in the extant art.

Using the compounds identified herein, the inventors have been able to substantially improve the performance of such commercially-available buffers, physiologic solutions, organ transport formulations and growth media. While the solutions buffers, growth media, and storage/transport solutions of the prior art are typically only able to maintain the necessary level of biological activity or cellular viability to permit storage of explanted tissues for a period of several hours to a few days post-harvest, the inventors have demonstrated surprising and unexpected results using the formulations disclosed herein. By supplementing such media with one or more tissue preserving/cellular viability prolonging compounds, the present invention now permits maintenance of biologic activity and/or cellular viability of explanted tissues even when stored under appropriate conditions for periods of time of from several days, to several weeks, and even up to and including several months post-harvest.

For example, the compositions of the present invention have been shown to prolong the survivability of explanted mammalian cells and tissues for periods of time of at least about 7 days (i.e., at least about 1 week), at least about 14 days (i.e., at least about 2 weeks), at least about 21 days (i.e., at least about 3 weeks), or even at least about 28 days (i.e., at least about 4 weeks or longer). In fact, in particular practice of the present invention, the cellular viability, biological activity, and/or organ function, the inventors have shown that explanted mammalian tissues may be stored under refrigeration conditions substantially in at least a first tissue viability-enhancing buffer/storage solution for periods of time of several weeks to several months while maintaining cellular viability, tissue integrity, and biological function sufficient for explantation of the tissue into selected animal recipients.

In various embodiments, where it is particularly desirable to maintain the harvested biological material (e.g., populations of cells, cell monolayers, and bilayers of in vivo or in vitro cultured cells, in vivo, ex vivo or ex situ derived mammalian tissues (including mammalian tissue-engineered constructs (i.e., TECs), tissue-engineered devices (i.e., TEDs) (see e.g., Baumert et al., 2006), tissue engineered products (TEPs) (see e.g., MacNeil, 2007; Campbell and Campbell, 2007), or mammalian organs or organ-derived tissues), the preservative compositions disclosed herein provide exceptional results, particularly for maintaining significant cellular viability in such biological samples for substantial periods of time (e.g., weeks to months post-harvest/collection/explantation). Importantly, the inventors have developed pharmaceutically-acceptable storage/transport compositions that permit retention of 60% or more (and even 65%, 70%, or 75% or more) of the initial post-harvest viability of a biological material when stored in such compositions and maintained under appropriate environmental conditions for extended periods of time. In illustrative embodiments, various biological materials may be prepared, stored, and transported under conditions that permit the harvested cells, tissues, or organs to retain significant viability (e.g., 75%, 80%, 85%, 90%, or 95% of their initial post-harvest viability) when compared to storage of similar biological samples in conventional buffers, organ transport solutions, or mammalian growth media alone.

Likewise, in certain other embodiments, where it is desirable to prepare populations of mammalian cells, tissue, tissue grafts, TCEs, TEDs, TEPs, or one or more explanted organ(s), which maintain substantial viability after initial preparation and subsequent storage, use of the disclosed tissue viability-preserving compositions effectively permit such cell(s), tissue(s), tissue graft(s), TCE(s), TED(s) TEP(s), or explanted organ(s) to remain substantially viable for extended periods of time, often from several days to several weeks, and even from several weeks to several months or more without substantial loss of viability of the biological material so maintained.

In various embodiments of the invention, it may be desirable to prepare populations of mammalian cells, tissues, or an organ, and to store them under conditions in which they remain at least about 60% viable, or otherwise biologically-functional, during, and/or immediately following, storage and/or transport in one or more of the compositions disclosed herein for a particular interval of time. In some cases, it may be desirable to store such populations of cells, tissues, or an organ under conditions in which they remain at least about 65% viable, at least about 70% viable, at least about 75% viable, at least about 80% viable, at least about 85% viable, at least about 90% viable, or even under conditions in which they retain substantially viable (i.e., at least about 90%, 91%, 92%, 93%, 94%, 95%, 96%, 97%, 98%, 99%, or greater for a period of time that may be on the order of a few minutes, a few hours, a few days, a few weeks, or even a few months or longer, depending upon the environmental conditions selected for storage, and the particular cell(s), tissue(s), or organ(s) being maintained in one or more of the storage/transport compositions disclosed herein.

Similarly, it may be desirable in the practice of the invention to prepare biological samples biological materials, and bioengineered products that retain at least about 50% or greater viability when processed according to the methods and processes described herein, and stored substantially in one or more of the compositions as provided by the present invention. In such instances, the present methods may be employed to facilitate prolonged tissue viability and enhanced implantation suitability for extended periods of time following which at least about 60%, at least about 65%, at least about 70%, at least about 75%, at least about 80%, at least about 85%, at least about 90%, or even at least about 95% or more of the tissue or organ remains viable, biochemically-functional, and/or otherwise medically-suitable for implantation.

It is also contemplated that the disclosed compositions will find particular utility in methods for preserving sufficient biological functional and retaining sufficient cellular viability and/or tissue integrity in poorly-perfusable mammalian tissues that have previously not been amenable to long-term storage. Through use of the present compositions, tissues that were previously only biologically-viable for implantation following short-term (e.g., several hours to several days) storage, may now be prepared that are substantially biologically active and amenable to intermediate-term (e.g., several days to several weeks) and even extended or long-term (e.g., several weeks to several months or more) storage. Such methods thereby significantly extend the conventional harvest-to-implantation "window of opportunity," and provide novel methods for extending the usable "shelf-life" of harvested tissues or cultured cell populations from several hours to many weeks to even several months or longer.

In particular embodiments, mammalian cells, tissues or organs that have been stored and/or transported under appropriate environmental conditions in one or more of the disclosed cellular viability-preserving storage compositions will preferably remain substantially viable during, and at least immediately following, storage in the compositions for periods of time of at least about 24 hours, at least about 48 hours, at least about 72 hours, at least about 96 hours, at least about 120 hours, at least about 144 hours, or even at least about 168 hours or more (corresponding, respectively, to periods of time of at least about 1 day, at least about 2 days, at least about 3 days, at least about 4 days, at least about 5 days, at least about 6 days, or even at least about 7 days or more).

In other aspects of the invention, and particular those in which it is desirable to preserve the cellular viability and/or biological activity and/or function of a population of mammalian cells, a mammalian tissue or organ, tissue engineered products and constructs, or other suitable biological material for even longer periods of time, the inventors have demonstrated that use of the disclosed tissue-viability-preserving compositions may facilitate both storage and transport of substantially viable biological material for periods of time of at least about 1 week, at least about 2 weeks, at least about 3 weeks, at least about 4 weeks, at least about 5 weeks, at least about 6 weeks, or even at least about 7 weeks (corresponding, respectively, to periods of time of at least about 7 days, at least about 14 days, at least about 21 days, at least about 28 days, at least about 35 days, at least about 42 days, and at least about 49 days).

In another aspect of the invention, a novel composition is provided for use in the practice of the tissue-viability-preserving methods disclosed herein. In an overall and general sense, such a composition will typically comprise, consist essentially of, or consist of, (a) a biological medium, buffer, or storage/transport solution suitable for prolonged contact with a biological tissue or explant; (b) at least a first PEG having an average molecular weight (MW) of about 600 Daltons (Da); (c) at least a second PEG having an average MW of about 3350 Da, wherein each PEG is present in the composition at a concentration of from between about 0.5% and 5% (vol./vol.); (d) at least a first chelating agent; and (e) at least a first antioxidant.

Similarly, the invention also provides compositions for extended storage of an in vitro or an ex situ animal tissue or organ under conditions that permit the tissue or organ to remain substantially viable and suitable for implantation. Such compositions will preferably comprise, consist essentially of, or consist of, (a) a pharmaceutically-acceptable biological medium, buffer, or storage solution; (b) at least a first polyethylene glycol (i.e., (poly(ethylene glycol)), abbreviated "PEG") having an average MW of about 600 Da; (c) at least a second PEG having an average MW of about 3350 Da (i.e., 3.35 kDa), wherein each of the PEG polymers is present in the medium, buffer, or storage/transport solution at a concentration of from between about 1% and 3% (vol./vol.); (d) at least a first antioxidant; and (e) at least a first metal chelating agent.

In another exemplary illustrative embodiment, the invention provides a composition that comprises, consists essentially of, or alternatively, consists of: (a) a pharmaceutically-acceptable biological medium, buffer, or storage/transport solution; (b) at least a first PEG having an average MW of about 600 Da; (c) at least a second PEG having an average MW of about 3350 Da, wherein each of the PEG polymers is present in the medium, buffer, or storage/transport solution at a concentration of about 1.1% to about 1.3% (vol./vol.); (d) at least a first antioxidant; and (e) at least a first metal chelating agent.

The invention also provides a method for extending the post-explantation viability of an explanted mammalian tissue or organ. In an overall and general sense, this method comprises, consists essentially of, or consists of, at least the step of maintaining the explanted mammalian tissue or organ in a pharmaceutically-acceptable storage solution that comprises at least one biochemical buffer or cell growth medium, at least one biomembrane sealing agent, at least one iron chelator, and at least one antioxidant, each of which is present in the composition in an amount effective to extend the post-explantation viability of a mammalian tissue or organ that is maintained in such a storage solution as compared to storage of the mammalian tissue or organ in the biochemical buffer or pharmaceutically-acceptable storage solution alone.

The invention also provides a method for intermediate- or long-term storage of harvested mammalian cells, tissue or organ prior to transplantation into a selected recipient animal. In an overall and general sense, the process comprises at least the steps of: (a) contacting the harvested mammalian cells, tissue or organ with a composition that comprises, consists essentially of, or alternatively consists of: (i) at least one biological buffer or mammalian cell growth medium; (ii) at least one biomembrane sealing agent; (iii) at least one iron chelator; and (iv) at least one antioxidant; and (b) maintaining the harvested mammalian cells, tissue or organ in the composition at a temperature of from between about −10° C. and about 30° C., substantially until transplantation of the cells, tissue or organ into the selected recipient animal, wherein the cells, tissue, or organ so maintained, will retain at least about 60% or more of its viability, biological function, tissue integrity, and/or transplantation suitability.

In this method, the harvested mammalian cells, tissue or organ preferably retains substantially at least about 60%, at least about 65%, at least about 70%, or at least about 75%, or greater viability after being maintained in the composition for a period of at least about 10 days, at least about 20 days, at least about 30 days, at least about 40 days, at least about 50 days, or even at least about 60 days or longer, depending upon the particular cell or tissue type to be stored, as well as the ambient environmental conditions under which the cells, tissue, or organ is stored.

During step (b) of the aforementioned method, it is also preferable that the harvested mammalian cells, tissue, or organ remain substantially at least 60% viable after being maintained in the composition under suitable environmental conditions, for a period of at least about 5 days, at least about 15 days, at least about 25 days, at least about 35 days, or at least about 45 days, or longer. Depending upon the particular tissue, cells, or organ, as well as the particular method of implantation employed, in step (b) of this method, it may be preferable that the stored mammalian cells, tissue, or organ remain substantially at least 70% viable after being maintained in the composition under suitable environmental conditions, for a period of at least about 10 days, at least about 20 days, at least about 30 days, at least about 40 days, or at least about 50 days, or longer.

Similarly, it may also be desirable in the practice of the invention to prepare tissue storage compositions that facilitate substantial cellular viability maintenance for particular cells, tissues, or organs maintained in one or more of the disclosed copositions under physiologically-acceptable environmental conditions such that at least 80% or more of the stored biological sample retains substantial cellular viability after being stored in the composition under suitable environmental conditions for periods of at least 7 days, at least about 14 days, at least about 21 days, at least about 28 days, or at least about 35 days, or longer.

Likewise, for the long-term storage of particularly resilient tissues (e.g., bone, tendon, ligament, cartilage, etc.) it may be desirable in the practice of the invention to prepare storage compositions that substantially prolong the cellular viability of the explained tissues under physiologically-acceptable environmental conditions such that at least 90% or even 95% or more of the cellular viability of the biological tissue is maintained following storage of the tissue in one of the disclosed viability-enhancing, tissue integrity-enhancing compositions. In certain situations, the inventors contemplate that such tissues may be maintained in storage under suitable environmental conditions for periods of at least a week, at least 2 weeks, at least 3 weeks, at least 4 weeks, or even at least 5 or more weeks without sa substantial loss of cellular function, or tissue integrity.

In another aspect, it is also desirable that the harvested mammalian cells, tissue, or organ preferably remains significantly viable, and in particular, substantially viable (i.e., at least about 90%, at least about 95%, at least about 96%, at least about 97%, at least about 98%, or at least about 99% or greater), during the interval in which the cells, tissue or organ is comprised, stored, transported, or perfused with one of the compositions disclosed herein.

Likewise, while the step of maintaining the harvested mammalian cells, tissues or organs in the composition preferably occurs substantially at a temperature of from between about −10° C. and about 20° C., in particular instances, the step of maintaining such cells, tissues or organs may be performed substantially in an ambient environment having a temperature of from between about 0° C. and about 15° C., and in many cases, preferably at an ambient storage temperature of from between about 4° C. and about 10° C.

In a further embodiment, the invention provides a composition that comprises, consists essentially of, or, alternatively, consists of: (a) a biological buffer, diluent, growth medium, storage solution, or organ transport medium; (b) at least one biomembrane sealing agent; (c) deferoxamine mesylate; and (d) at least one antioxidant. Preferably each of the compounds of (b)-(d) is present in the formulation in amounts effective to prolong the viability of a biological cell, tissue or organ that is maintained or stored in the composition, as compared to maintenance of the biological cell, tissue, or organ stored in the biological buffer, growth medium, tissue storage or organ transport solution alone.

In illustrative embodiments the biomembrane sealing agent comprises at least a first PEG, and may optionally further comprise one or more additional biomembrane sealing compounds. In certain embodiments, the additional compound is a second PEG that has a distinctly different average MW than the first PEG. Preferably the PEGs employed in the practice of the invention have an average MW of from about 50 Da to about 50,000 Da (i.e., 50 kDa), with an average MW in the range of about 100 Da to about 10 kDa being preferable.

In formulating the claimed tissue viability-preserving compositions, the biomembrane sealing agent is present in the composition at a concentration of between about 0.001% (vol./vol.) and about 50% (vol./vol). Alternatively, the biomembrane sealing agent may be present at a concentration of between about 0.01% (vol./vol.) and about 30% (vol./vol.), and preferably present in the formulation at a concentration of between about 0.50% (vol./vol.) and about 10% (vol./vol).

In one application of the disclosed preservation methods, the biomembrane sealing agent may comprise a mixture of at least one lower-MW PEG (e.g., a PEG having an average MW of from about 50 Da to about 2 kDa) and at least one higher-MW PEG (e.g., a PEG having an average MW of from about 2 kDa to about 50 kDa). In particular formulations each of the lower- and higher-MW PEGs is present in the composition at a concentration of between about 0.1% and about 20% (vol./vol.), and preferably each is present at a concentration of between about 1.0% and about 10% (vol./vol.). In one formulation, the lower-MW PEG preferably has an average MW of about 600 Da, and the higher-MW PEG preferably has an average MW of about 3.35 kDa, with the former being present in the composition at a concentration of about 1.3% and the latter being present in the composition at a concentration of about 1.5%.

In various embodiments, the composition may comprise, consist essentially of, or consist of: (a) at least one PEG at a final concentration of between about 0.01% (vol./vol.) and about 30% (vol./vol); (b) deferoxamine mesylate at a final concentration of between about 0.1 µM and about 10 µM; and (c) ascorbic acid at a final concentration of between about 0.010% (vol./vol.) and about 0.10% (vol./vol.).

In additional embodiments, the composition comprises, consists essentially of, or, alternatively, consists of: (a) PEG-600 or PEG-3350 at a final concentration of between about 0.01% (vol./vol.) and about 10% (vol./vol); (b) deferoxamine mesylate at a final concentration of between about 0.01 µM and about 100 µM; and (c) ascorbic acid at a final concentration of between about 0.0010% (vol./vol.) and about 1.0% (vol./vol.).

Similarly, in related embodiments, the composition may comprise, consist essentially of, or, alternatively, consist of: (a) PEG-3350 at a final concentration of between about 0.1% (vol./vol.) and about 10% (vol./vol); (b) an iron chelator, such as deferoxamine mesylate, at a final concentration of between about 0.01 µM and about 100 µM; and (c) an antioxidant (such as, e.g., 2,6-di-tert-butyl-4-methylphenol (BHT) or ascorbic acid), at a final concentration of between about 0.001% (vol./vol.) and about 0.20% (vol./vol.).

Likewise, in another illustrative embodiment, the tissue viability-sustaining compositions of the present invention may comprise, consist essentially of, or, alternatively, consist of: (a) PEG-600 and PEG-3350, each at a final concentration of between about 1.0% (vol./vol.) and about 5% (vol./vol); (b) a chelator, such as deferoxamine mesylate, preferably at a final concentration of from between about 0.1 µM and about 10 µM; and (c) an antioxidant (such as, e.g., 2,6-di-tert-butyl-4-methylphenol or ascorbic acid), preferably at a final concentration of from between about 0.010% (vol./vol.) and about 0.10% (vol./vol.)

Another aspect of the invention is a process for prolonging the viability of a population of mammalian cells or tissues stored for extended, or prolonged periods in one or more commercially available biological media, biochemical buffers, or an organ storage/transport solution. In an overall sense, this process generally involves at least the steps of:

a) aseptically supplementing a commercially-available biological medium, biochemical buffer, diluent, growth medium, or organ storage/transport solution with effective amounts of (i) at least one biomembrane sealing agent; (ii) at least one chelator; and (iii) at least one antioxidant; and b) maintaining a population of mammalian cells or a mammalian tissue or organ in the aseptically-supplemented biological medium, biochemical buffer, or organ storage/transport solution, at a temperature of from between about −10° C. and about 25 to 30° C. (and more preferably at a temperature of from between about 0° C. and about 15 to 20° C.), wherein the population of mammalian cells or mammalian tissue or organ so maintained is between about 60 and about 100% viable during storage in the supplemented medium, buffer, diluent, or storage solution, for a period of time of at least about 7 days (or more preferably, a period of time of at least about 14 days, at least about 21 days, or at least about 28 days or longer) under conditions of refrigeration or near-freezing that effectively prolong the viability of the cells, tissues or organs, far beyond what is conventionally possible using only un-supplemented medium, buffer, or organ storage/transport solution.

While the methods and compositions of the present invention are contemplated to be useful in the storage and viability-preserving function of a variety of animal cells, tissues, and organs, such methods and compositions are particularly suited for the harvest, storage and transport of mammalian cells, tissues and organs. Especially relevant are those cells, tissues, or organs that are harvested from suitable living or cadaveric donor mammals and are destined for implantation into suitable mammalian recipients.

Exemplary types of mammalian cells which may be harvested, stored, and/or transported using one or more of the methods and compositions described herein include, but are not limited to: chondral cells, cartilagenous cells, osteochondral cells, islet cells, osteogenic cells, neural cells, bone cells, bone marrow cells, adipose cells, fibroblasts, muscle cells, blood, blood components, stem cells, and embryonic stem cells.

Exemplary types of mammalian tissues which may be harvested, stored, and/or transported according to the present invention include, but are not limited to, skin, cartilage, tendons, ligaments; fascia, tibialis, patellas and other bones, heart valves, semi-tendinous tissues, blood vessels, vertebral discs, corneas, lenses, meniscus, hair, adipose tissue, fibrous tissue, neural tissue, connective tissue, and striated, smooth or cardiac muscle tissue.

Explanted animal tissues, cell populations, and harvested mammalian organs prepared by any one of the methods or processes disclosed herein, or any explanted mammalian cells, tissue, or organ stored in one or more of the disclosed compositions are preferably suitable for implantation into a selected recipient animal, and particularly into a selected recipient mammal. Examples of mammalian species into which the explanted tissue may be transplanted, include, but are not limited to, humans, cattle, horses, sheep, pigs, goats, rabbits, dogs, cats, and non-human primates In yet another aspect, the present invention also provides an explanted, substantially-viable, mammalian tissue or organ that is prepared by any one of the aforementioned processes. Such explanted tissue or organ is preferably of bovine, canine, caprine, equine, feline, galline, human, lapine, leporine, lupine, murine, ovine, porcine, vulpine, or non-human primate origin, with porcine and human explants being particularly preferred. The mammalian tissue or organ may be obtained from a living or cadaveric donor, and optionally may be derived from a genetically-modified, non-human animal.

While the methods and compositions of the present invention are contemplated to be useful in the storage and viability-preserving function of a variety of cell and tissue types, in particular embodiments, use of the disclosed method in the storage and/or transport of animal cells and tissue types are particularly desirable. In the context of this invention, exemplary types of mammalian cells and tissues (a) for which the disclosed compositions may be used to store and/or transport such cells or tissues; or (b) for which the disclosed methods may be employed to prolong cellular function and/or viability of such stored cells or tissue (inter alia, ex vivo biologic activity, ex situ tissue integrity, and/or in vitro storage or transport) may include (but are expressly not limited to): (i) one or more animal (and particularly, mammalian), cell types selected from the group consisting of chondral, cartilagenous, osteochondral, islet, osteogenic, neural, bone, bone marrow, adipose, fibroblast, muscle, blood, and stem cells; (ii) one or more animal tissues selected from the group consisting of skin, bone, cartilage, tendon, ligament, vertebral disc, cornea, lens, meniscus, hair, striated muscle, smooth muscle, cardiac muscle, adipose tissue, fibrous tissue, neural tissue, and connective tissue; or (iii) one or more mammalian organs selected from the group consisting of cochlea, testis, ovary, stomach, lung, heart, liver, pancreas, kidney, intestine, and eye.

Cell populations, tissues and organs prepared by the processes provided herein may be of any origin, although those of animal origin and of mammalian origin in particular, are preferable. Exemplary explanted biological materials may be obtained from one or more animals, including, but not limited to, bovines, canines, caprines, equines, felines, gallines, humans, lapines, leporines, lupines, murines, ovines, porcines, vulpines, or non-human primates.

Apart from the particular parameters described herein, in certain embodiments, it is also contemplated that the selection of appropriate experimental parameters or storage conditions (e.g., for example, environmental or ambient temperature, atmospheric pressure, partial pressure of one or more ambient gases (e.g., nitrogen [$N_2$], oxygen [$O_2$], argon [Ar], or carbon dioxide [$CO_2$]), sterility of the compositions, and skills such as aseptic techniques and handling of the compositions and tissue samples, and other such like parameters is well within the purview of the skilled artisan in the field, having benefit of the present Specification, and that such common tissue handling, storage, and transport techniques and parameters need not be further explained herein.

As a general guide, however, the inventors contemplate that tissue storage and tissue handling methodologies that are currently employed for short-term tissue storage, transport, and implantation, etc. may readily be adapted for use in practice of the methods of the present invention that provide for the first time, compositions for maintaining tissue integrity and cellular viability when such tissues are prepared for intermediate- and longer-term tissue storage regimens. It is further contemplated that standard laboratory techniques for harvesting, preparing, handling, storing, transporting, and implanting of tissues and organs using conventional biological buffers, growth media, and organ storage and transport solutions (which currently limit the "window" of harvest-to-transplantation to periods of several hours to several days) may be adapted and modified using the compositions and methods described herein, to substantially increase the post-explant tissue and organ viability "window" to periods of time that range from many hours, to many days, and even to periods of time of several months, and perhaps even longer for certain tissue types, storage conditions, and storage solution formulations.

The inventors contemplate that the skilled artisan, having benefited from the teachings provide herein, would be able to make and use a variety of preservation compositions that comprise one or more of the active compounds as described herein.

4.1 Conventional Culture, Storage and Transport Solutions

It is contemplated that beneficial effects will be achieved by supplementing a conventionally-available buffer or storage solution with one or more of the active compounds described herein (e.g., supplementation of an existing growth medium or buffer with an effective amount of at least a first biomembrane sealing agent).

Commercially available, and/or conventional organ and tissue transport or storage solutions contemplated to be useful in the preparation of the improved compositions of the present invention. include, but are not limited to, saline, phosphate-buffered saline, lactated Ringer's solution, parenteral solutions, Eagle's minimal essential medium (EMEM); Dulbecco/Vogt's Modified Eagle's minimal essential medium (DMEM); Moore's Roswell Park Memorial Institute essential medium (RPMI), RPMI-1640, and related RPMI-derived media (Cambrex); Fisher's medium, Glasgow's modified essential medium (G-MEM); minimal essential medium (MEM); serum-free lymphocyte medium (AIM-V®) (Invitrogen Corp., Carlsbad, Calif.), Neurobasal® medium (Invitrogen Corp.), GlutaMAX® (Invitrogen Corp.), Iscove's Modified Dulbecco's Medium (IMDM) (HyClone, Logan, Utah); and other similar formulations which may be obtained from a variety of commercial suppliers including, for example, BD (Becton, Dickinson and Company; Franklin Lakes, N.J.); Mediatech, Inc. (Herndon, Va.); Cambrex Corporation (East Rutherford, N.J.); Sigma Chemical Co. (St. Louis, Mo.); BioVeris Corp. (Salinas, Kans.); and MP Biomedicals, Inc. (Solon, Ohio).

Likewise, exemplary organ or tissue transport buffers to which the tripartite active compounds may be added include, but are not limited to, commercially-available formulations such as ViaSpan© (Belzer UW solution, Barr Laboratories, Inc., Pomona, N.Y.), Optisol©, Optisol-GS and DexSol© storage media (Chiron Ophthalmics, Irvine, Calif.), McCarey-Kaufman medium, K-Sol medium (Cilco, Huntington, W. Va.), or combinations or derivatives thereof.

4.2 Biomembrane Sealing Agents

In each of the foregoing methods, the tissue preserving/cellular viability-enhancing compositions comprise, consist essentially of, or, alternatively, consist of: (a) a biological medium, biochemical buffer, organ storage/transport solution; and (b) at least a first biomembrane-sealing agent in an amount, effective to extend, lengthen, or prolong the post-harvest and/or pre-implantation viability of an explanted population of mammalian cells, tissue or a harvested mammalian organ.

Biomembrane-sealing agents of various MWs have been utilized for nearly four decades as adjuncts to culture media for their ability to protect cells against fluid-mechanical injuries. These agents include for example, hydrophilic polymers such as poly (oxyethylene) (POE), poly (alkylene glycol) (PAG), poly (ethylene glycol) (PEG), poly (ethylene oxide) (PEO), polyvinyl alcohol (PVA), amphipathic polymers including, but not limited to, pluronics, poloxamers (including poloxamer P-188 [aka CRL-5861 and available from CytRx Corp. (Los Angeles, Calif.)], as well as methylcellulose, sodium carboxymethyl cellulose, hydroxyethyl starch (HES), polyvinyl pyrrolidine (PVP), and dextrans. Some biomembrane-sealing agents including HES and PEG have shown effective cryopreservative abilities in various organ transplantation studies.

The term "biomembrane-sealing agent" has been broadly used herein to define a broad class of compounds that have similar properties of interest. In the context of the present invention, exemplary biomembrane-sealing agents include, but are not limited to, one or more compounds selected from the group consisting of poly(ethylene glycol) (PEG), a block copolymer containing a polyalkylene glycol, tri-block containing a polyalkylene glycol, a block copolymer containing a polyalkylene oxide, tri-block containing a polyalkylene oxide, polyvinyl alcohol, polyvinyl pyrrolidone, dextrans, hyaluronic acid, hyaluronate, poloxamine, pluronic polyols, dimethylsulfoxide, starch, HES, cellulose, sodium carboxymethyl cellulose, poly(polyethylene glycol methacrylate), poly(glycerol methacrylate), poly(glycerol acrylate), poly(polyethylene glycol acrylate), poly(alkyl oxazoline), phosphoryl choline polymers, sodium and potassium polymethacrylate, sodium and potassium polyacrylate, polymethacrylic acid and polyacrylic acid and combinations thereof. In the routine practice of the present invention, the inventors believe that particularly effective biomembrane sealing agents will generally comprise one or more such compounds, and will preferably have an average MW of between about 50 Da and about 200 kDa, although it is not an absolute requirement that the sealing agent necessarily have an average MW solely within these ranges. In the case of polymers, the inventors contemplate that a number of biomembrane sealing agents (e.g., PEGs and such like) may be effectively employed in the disclosed methods, even if such compositions comprise a plurality of polymer compounds that differ in their individual average MWs. It is also contemplated that in a number of formulations, the sealing agent may comprise at least 2, at least 3, or even at least 4 or more polymers (each having distinctly different average MWs). Such combinations of multi-MW polymers are explicitly considered to be within the scope of the present teaching.

Moreover, when one or more such biomembrane sealing agents is included in the formulation of a tissue preservative composition as described herein, the inventors contemplate that the quantity, size, and molecular ranges of such agents need not be present in the final composition in equal amounts. However, it will generally be understood that such compounds will most often be present in the tissue preservative/storage/transport solutions at final (i.e., "working") concentrations that are in the range of between about 0.001% (vol./vol.) and about 60% (vol./vol.). In particular formulations, the selected biomembrane sealing agent(s) may even be present in the tissue preservative/storage/transport solution at a working concentration of between about 0.01% (vol./vol.) and about 50% (vol./vol.), or even more particularly, at a final concentration of between about 0.10% (vol./vol.) and about 40% (vol./vol.), or even more particularly still, at a final concentration of between about 0.20% (vol./vol.) and about 30% (vol./vol.). Such ranges, of course, are exemplary, are should not be considered scope limiting. All intermediate ranges and all intermediate integer values within a stated range herein are inherently included within the scope of the present teaching, as are all equivalent concentrations of the recited compound(s) even if the concentration is expressed as % weight/volume (wt./vol), % weight/weight (wt./wt.), or by conventional S.I. units e.g., millimolar and micromolar (mM and µM, respectively).

As detailed herein and elsewhere[1], the inventors and their co-workers have described in various embodiments the use of one or more PEG compound(s) as biomembrane sealing agent(s) in the practice of the invention; particularly the use of one or more PEGs having an average MW of from about 50 Da to about 50 kDa. In other embodiments, the use of one or more PEGs having an average MW of from about 100 Da to about 10 kDa, or still more particularly, from about 500 Da to about 5 kDa including, but not limited to, e.g., PEGs having an average MW of about 600 Da, and/or PEGs having an average MW of about 3350 Da.

Poly (ethylene glycols) (PEGs) and poly(ethylene oxides) (PEOs) are long-chain organic polymers or oligomers that are composed of repeating subunits of identical ethylene oxide monomers. Chemically they are represented as

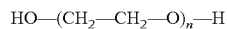

$$\text{HO—(CH}_2\text{—CH}_2\text{—O)}_n\text{—H}$$

where n is the number of repeating ethylene glycol monomers comprising the polymer. Although the terms PEG and PEO are chemically synonymous, historically the term PEG has been used to describe relatively shorter polymers while PEO has typically referred to relatively longer ethylene glycol polymers.

PEGs find utility in a number of biological applications, and can be broadly divided into two types: a) polymeric PEG-based chains having average MWs ranging from about 1 kDa to ≥20 kDa; and 2) PEG-like chains with average MWs usually on the order of ≤1 kDa.

While PEGs and PEOs of differing average MWs have different physical properties (e.g., viscosity, melting point, etc.) due to chain length effects, their chemical properties are nearly identical, regardless of the average MW of the polymers. PEG and PEO derivatives are also ubiquitous, with the most common derivative being the methyl ether (methoxypoly (ethylene glycol)), which is usually abbreviated as "mPEG."

Most PEGs and PEOs are polydisperse i.e., the polymers exist over a wide range of molecular masses—a characteristic of many synthetic polymeric materials. The size distribution can be characterized statistically by its average molecular weight (abbreviated MW), its "weight average molecular weight" (abbreviated $M_w$) or its "number average molecular weight" (abbreviated $M_n$), the ratio of the latter of which, ($M_w/M_n$), is called the "Polydispersity Index" (PDI). Both $M_w$ and $M_n$ can be accurately measured for polymers using either conventional or matrix-assisted laser desorption/ionization (MALDI) time-of-flight (TOF) mass spectroscopy.

The numbers that are often included in the names of PEGs and PEOs (e.g., PEG-10,000, PEG-4000, or PEG-600, etc.) indicate the average MWs of the various PEG polymers present in the compound. For example, a population of PEG polymers with a size distribution centering around an average MW of ≈3500 Da, would generally comprise a distribution of PEG polymers whose mean was around n≈80 monomers/polymer, and this population of polymers would typically be labeled "PEG 3500" or "PEG-3500"[2]

[2]For additional information concerning the nomenclature and physical properties of various PEG and PEO compounds, see, e.g. Aldrich and Kumar, PCT. Intl. Pat. Appl. Publ. Ser. No. WO2002042259 and U.S. Pat. No. 7,038,078; each of which is specifically incorporated herein by reference in its entirety.

Moreover, when one or more such biomembrane sealing agents is included in the formulation of a tissue preservative composition as described herein, the inventors contemplate that the quantity, size, and molecular ranges of such agents need not be present in the final composition in equal amounts. However, it will generally be understood that such compounds will most often be present in the tissue preservative/storage/transport solutions at final (i.e., "working") concentrations that are in the range of between about 0.001% (vol./vol.) and about 60% (vol./vol.). In particular formulations, the selected biomembrane sealing agent(s) may even be present in the tissue preservative/storage/transport solution at a working concentration of between about 0.01% (vol./vol.) and about 50% (vol./vol.), or even more particularly, at a final concentration of between about 0.10% (vol./vol.) and about 40% (vol./vol.), or even more particularly still, at a final concentration of between about 0.20% (vol./vol.) and about 30% (vol./vol.). Such ranges, of course, are exemplary, are should not be considered scope limiting. All intermediate ranges and all intermediate integer values within a stated range herein are inherently included within the scope of the present teaching, as are all equivalent concentrations of the recited compound(s) even if the concentration is expressed as % weight/volume (wt./vol), % weight/weight (wt./wt.), or by conventional S.I. units e.g., millimolar and micromolar (mM and μM, respectively).

4.3 Antioxidants

Suitable antioxidants for the practice of the present invention, include, for example, but are not limited to, one or more compounds selected from the group consisting of 2-tert-butyl-4-hydroxyanisole, 3-tert-butyl-4-hydroxyanisole, or combinations thereof (e.g., butylated hydroxyanisole, BHA); 2,6-di-tert-butyl-4-methylphenol [a.k.a., butylated hydroxytoluene (BHT)], 2,6-di-tert-butyl-p-cresol, (DBPC); ascorbic acid; ascorbate; α-tocopherol; ubiquinol-6; ubichromenol-6; α-tocopherol hydroquinone; α-tocopherol acetate; β-carotene (3,7,12,16-tetramethyl-1,18-bis(2,6,6-trimethyl-1-cyclohexenyl)-octadeca-1,3,5,7,9,11,13,15,17-nonaene); vitamin A (retinol); vitamin B1 (thiamine); vitamin B2 (riboflavin); vitamin B3 (niacin); vitamin B5 (pantothenate); vitamin B6 (pyridoxine/pyridoxal); vitamin B7 (biotin); vitamin B9 (folic acid); vitamin B10 (p-aminobenzoic acid); vitamin B12 (cobalamin/dibencozide); and one or more green tea extracts (including e.g., but not limited to, (−)epigallocatechin-gallate; (−)gallocatechin-gallate; (−)epicatechin-gallate; (−)epigallocatechin; (+)gallocatechin; (−)epicatechin; and (−)catechin).

In particular illustrative embodiments, the antioxidant comprises ascorbic acid. In various embodiments, the compositions of the present invention will preferably comprise at least one antioxidant at a concentration of between about 0.001% and about 1.0% (vol./vol.), and even more particularly at a concentration of between about 0.010% and about 0.10% (vol./vol.). In particular embodiments, the compositions of the present invention will preferably comprise at least two antioxidants, each present in the composition at a concentration of from between about 0.0001% and about 1.0% (vol./vol.). More particularly, such antioxidant compounds may be present in the final compositions at a concentration of between about 0.0010% and about 0.0% (vol./vol.).

In other formulations of the present compositions, the inventors contemplate the use of 2,6-di-tert-butyl-4-methylphenol as an antioxidant in the tissue preservation-enhancing compositions. In such embodiments, 2,6-di-tert-butyl-4-methylphenol is preferably present in the composition at a final concentration of between about 0.00003% (wt./vol.) and about 3.0% (wt./vol.), or even more particularly, at a final concentration of between about 0.0003% (wt./vol.) and about 0.3% (wt./vol.), or even more particularly still, at a final concentration of between about 0.003% (wt./vol.) and about 0.03% (wt./vol.). Such ranges, of course, are exemplary, are should not be considered scope limiting, and as indicated supra, all intermediate ranges and all intermediate integer values within a stated numerical range herein are inherently included within the scope of the present teaching, as are all equivalent concentrations of the recited compound(s) even if the concentration is expressed as % wt./vol, % wt./wt., or by conventional S.I. units (including, e.g., mM, μM, etc.).

4.4 Chelators

The term "chelator" is used broadly to describe a compound that is capable of binding to one or more metal cations (including e.g., but not limited to: sodium [$Na^+$], magnesium [$Mg^{++}$], calcium [$Ca^{++}$], zinc [$Zn^{++}$], and iron [$Fe^+$, $Fe^{++}$, and $Fe^{+++}$] ions). Exemplary chelating agents include, for example, but are not limited to, those compounds such as deferoxamine mesylate, 2,2'-dipyridyl, and 1,10-phenanthroline, EDTA, EGTA, diaminoethane, and the like. In illustrative embodiments, the use of deferoxamine mesylate has been shown to be highly effective in the chelation of iron in compositions comprising the agent.

The compositions of the present invention will preferably comprise at least one chelator at a concentration of between about 0.001 μM and about 1 mM, more particularly, at a concentration of between about 0.01 μM and about 100 μM, and more particularly still, at a concentration of between about 0.10 μM and about 10 μM.

In exemplary embodiments, the iron chelator, deferoxamine mesylate, has been employed in the preparation of tissue viability-preserving formulations that show surprising and unexpected ability to substantially preserve the viability of mammalian tissues for periods of at least four, five, or even six weeks or longer.

4.5 Optional Supplements

The compositions disclosed herein may also be formulated to optionally comprise one or more additional components, including for example, pharmaceutically-acceptable salts (including e.g., the acid addition salts formed with the free amino groups of a protein or peptide), organic acids (including, e.g., acetic acid, oxalic acid, tartaric acid, citric acid, malic acid, fumaric acid, mandelic acid, succinic acid, and the like). Salts formed with free carboxyl groups of amino acids can also be derived from inorganic bases such as, for example, sodium, potassium, ammonium, calcium, or ferric hydroxides, and such organic bases as isopropylamine, trimethylamine, histidine, procaine, and the like.

The tissue viability-prolonging storage compositions of the present invention may also optionally be formulated to comprise one or more solvents, co-solvents, vehicles, diluents, buffers, growth media, storage media, carrier solutions, suspensions, colloids, and such like.

Similarly, in certain applications of the disclosed compositions and methods it may also be desirable to formulate one or more tissue viability-preserving compositions that further optionally comprise one or more of the following a pH stabilizer, a rheological agent, a sugar (including e.g., but not limited to, allose, arabinose, atrose, cellobiose, erythrose, erythrulose, fructose, fucose, furanose, galactose, glucose, gulose, idose, inulose, lactose, lactulose, levulose, lyxose, maltose, mannose, rhaffinose, rhamnose, ribose, ribulose, sialose, sucrose, talose, threose, trehalose, xylose, and xylulose), an alcohol (including e.g., but not limited to, ethanol, propanol, isopropanol, and PVA), a sugar alcohol (including e.g., but not limited to: adonitol, arabitol, dulcitol, erythritol, inositol, isomalt, lacitol, maltitol, mannitol, sorbitol, and xylitol), an inorganic salt (including e.g., but not limited to: NaCl, NaPO$_4$, CaPO$_4$, KCl, etc.), lycopene, proanthocyanidin, a surfactant, a preservative, a wetting agent, serum (including, e.g., but not limited to: fetal, adult, bovine and human serum), a serum substitute, an osmotic agent, or an antifoam compound.

The compositions of the present invention may also be optionally formulated by the addition of one or more compounds selected from the group consisting of: organic acids (including, e.g., but not limited to: citric acid, malic acid, succinic acid), starches (including, e.g., but not limited to: hydroxyethyl starch [HES]), vitamins, hormones (e.g., insulin), a pro-drug, a nuclease inhibitor, a kinase inhibitor, an antimicrobial agent (including, e.g., but not limited to: microbicides, mildewcides, fungicides, batericides, viricides, antimycotics, antihelminths, and such like), trophic factors, anti-inflammatory agents, steroids, cytokines, neurotrophins, serpins, interleukins, activin, α1-antitrypsin (AAT), α1-antichymotrypsin (AACT), α2-antiplasmin (AAP), brain-derived neurotrophic factor (BDNF), bone morphogenic proteins (BMPs) (including inter alia, BMP-1, BMP-2, BMP-3, BMP-4, BMP-5, BMP-6, BMP-7, BMP-8a, BMP-8b, BMP-9, BMP-10, BMP-15, as well as recombinant BMPs, including recombinant human BMPs [rhBMPs] such as rhBMP-2), colony stimulating factors (CSFs), cementum-derived growth factor (CGF), ciliary neurotrophic factor (CNTF), decorin, elafin, epidermal growth factor (EGF), erythropoietin (Epo), fibroblast growth factors (FGFs), glycosyl phosphatidylinositol, granulocyte-colony stimulating factor (G-CSF), growth differentiation factor (GDF), glial cell line-derived neurotrophic factor (GDNF), inhibins, insulin-like growth factor-I (IGF-I), insulin-like growth factor-II (IGF-II), integrin, interferon-γ (INF-γ), interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), leptin, mitogen activated protein kinase (MAPK), nerve growth factors (NGFs), pigment epithelium derived-factor (PEDF), phospholipase C, platelet-derived growth factor (PDGF), skin-derived anti-leukoproteinase (SKALP), transforming growth factor-α (TGF-α) or one or more additional members of the TGF "superfamily," (including, e.g., transforming growth factor-β [TGF-β], TGF-β1, TGF-β2, TGF-β3, TGF-β4, and TGF-β5), tumor necrosis factor-α (TNF-α), tumor necrosis factor-β (TNF-β), vascular endothelial growth factor (VEGF), etc.

The compositions of the present invention may also optionally formulated to comprise one or more compounds involved in maintaining cellular function, preserving cellular integrity, or maintaining the differentiated state of a given population of cells.

4.6 Maintenance of Cellular Viability, Tissue Function, and Organ Integrity

Preferably the populations of animal cells, and explanted mammalian tissues and/or organs stored and/or transported in one or more of the tissue preservative compositions disclosed herein, will comprise at least about 30% viable (i.e., living) cells as determined using the ratio of living to non-living cells quantitated using the live/dead fluoromicroscopic assay described above. More preferably, populations of animal cells, and explanted mammalian tissues and/or organs stored and/or transported in one or more of the tissue preservative compositions disclosed herein will comprise at least about 40% viable cells, or even at least about 50%, at least about 60%, at least about 70%, at least about 80%, or even more viable cells as determined by one or methods known in the art for assessing cellular viability (including, e.g., a live/dead fluoromicroscopic assay).

In certain embodiments, it may be desirable to obtain populations of animal cells or mammalian tissue grafts or explanted mammalian organs, which after storage and/or transport in one or more of the tissue preservative compositions disclosed herein, under conditions which provide for the viability of such cells, tissues, or organs, comprise at least about 85%, at least about 90%, at least about 95%, or even at least about 98% viable cells. In such methods, the resulting population of cells, tissues, or organs stored and/or maintained and/or transported in the disclosed tissue viability-preserving compositions of the present invention, will be substantially viable for a sufficient period of time to store, transport, or use the tissues, cells, or organs prepared using the methods disclosed herein. In those conditions, a tissue or population of cells that is "substantially viable" includes, but is not limited to those tissues and/or populations of animal cells, that when stored, maintained, and/or transported in one or more of the compositions disclosed herein, that are at least about 95% viable, at least about 96% viable, at least about 97% viable, at least about 98% viable, or even at least about 99% viable.

4.7 Pharmaceutically-Acceptable Compositions and Formulations

It is contemplated that tissue preservative solutions may be formulated that comprise, consist essentially of, or consist of the active compounds disclosed herein, in suitable quantities, either formulated as "end-user," "active" or "working" solutions, or alternatively, prepared in the form of one or more concentrated "stock" solutions that may subsequently be diluted into an appropriate solvent, buffer, or growth/transport medium to prepare final "working" solutions. For example, a concentrated stock solution that comprises the active ingredients (e.g., a biomembrane sealing agent; an antioxidant, and an iron chelator) in a 5×, 10×, or even 100×, concentration may be prepared and formulated for commercial sale. Such stock solutions may then be subsequently diluted five-, ten-, or one-hundred-100-fold, respectively, by an end-user into a suitable biological buffer, commercially-available organ transport solution, or growth medium to produce the final "working" solutions with each of the active ingredients in the correct amount for use by the practitioner.

Alternatively, the compositions of the present invention may be formulated for packaging and/or commercial sale as a ready-to-use solution, either alone, or optionally supplemented with one or more various additional ingredients as enumerated herein, and may be sterilized or pasteurized prior to sale or use using one of the conventional fluid sterilization/pasteurization means known in the art, such as for example, by autoclaving, irradiation, ultrafiltration, or such like.

In certain embodiments, the compositions may be formulated as sterile solutions, or alternatively, as sterilized powders by lyophilization or freeze-drying of the formulations using conventional methodologies. In the case of compositions that comprise large MW biomembrane sealing agents that are un-amenable to heat sterilization, it may be necessary to formulate the final working compositions from a powder or solid of the active ingredient, which may be later reconstituted and or filter sterilized or irradiated to form the final sterile composition.

The final storage/working solutions may be mixed aseptically at time of use, pre-mixed prior to sale and delivered as a ready-to-use, or ready-to-dilute product, or, alternatively, the solution or plurality of individual reagent solutions delivered as is, which are then reconstituted/mixed under non-sterile conditions by the end-user, and then at time sterile filtered immediately prior to use.

4.8 Tissue Viability-Enhancing Storage Compositions

The compositions disclosed herein may also be formulated to optionally comprise one or more additional ingredients, including for example, pharmaceutically-acceptable salts, including the acid addition salts (formed with the free amino groups of a protein or peptide) or such organic acids as acetic, oxalic, tartaric, citric, mandelic, and the like may also form one or more of the components of the storage/transport solution. Salts formed with free carboxyl groups of amino acids can also be derived from inorganic bases such as, for example, sodium, potassium, ammonium, calcium, or ferric hydroxides, and such organic bases as isopropylamine, trimethylamine, histidine, procaine and the like.

The compositions of the present invention may also optionally comprise one or more solvents, co-solvents, vehicles, diluents, buffers, growth media, storage media, carrier solutions, suspensions, colloids, and such like that comprise the active ingredients of the invention. The use and formulation of such compositions will be known to one of skill in the medical arts, particularly in the field of transplantation medicine, upon a fair reading of the instant specification.

Preferably, the population of mammalian cells or mammalian tissue so maintained is between about 60% and about 100% viable during storage in the supplemented medium, buffer, or storage solution, for a period of time of at least about 7 days (or more preferably, a period of time of at least about 14 days, at least about 21 days, or at least about 28 days or longer) under conditions of refrigeration or near-freezing that effectively prolong the viability of the cells, tissues or organs, far beyond what is conventionally possible using existing un-supplemented media, buffers, or storage/transport solutions alone.

In each of the methods described herein, It is preferable that the stored population of harvested cells, tissue(s) or organ(s) will retain at least about 70%, more preferably at least about 75%, still more preferably at least about 80%, or even more preferably at least about 85% or more of their pre-harvest (or immediately post-explant) viability following extended periods of storage in one or more of the tissue viability-enhancing compositions described herein. It is further preferable that the stored populations of cells, tissue(s) or organ(s) will retain at least about 90%, or even more preferably at least about 95% of their pre- or immediately post-harvest viability following even longer periods of storage in one of the disclosed compositions. For examples, in various embodiments, it is contemplated that the harvested biological material may remain in the composition under appropriate conditions for a period of at least 24 to 48 hours or longer (including, but not limited to, periods of at least 48 to 96 hours or longer, periods of at least 96 to 120 hours or longer, and even periods of at least 2 or 3 weeks or more), and still retain enough tissue integrity, cellular viability, and biological function to permit transplantation of the biological explant material even days, weeks, or months after initial tissue or organ harvesting.

In particular embodiments, it is contemplated that depending upon the particular tissue type, or particular organ stored, the compositions of the present invention will significantly increase the window of opportunity between harvest and implantation of the harvested biological material. Preferably, an explanted mammalian tissue or organ stored in such a composition will remain suitable for implantation for a period of at least 2 to 5 days or longer, more preferably for at least 5 to 10 days or longer, or even more preferably, at least 10 to 20 days or longer. Preferably, the explanted tissue or organ will retain a significant amount of cellular viability upon extended storage post-harvest, and it is preferable that the integrity and biochemical function of the store explant or organ will each substantially remain after storage in one of the disclosed compositions. In such instances, it is preferably that at least about 70% of the tissue or organ's pre-harvest tissue integrity, biochemical function, or metabolic activity is retained during storage of the tissue or organ, such that upon transplantation, the tissue or organ is functional when implanted into the recipient host.

Likewise, it is also preferable that at least about 75%, at least about 80%, at least about 85%, or even at least about 90% or more of the tissue or organ's pre-harvest tissue integrity, biochemical function, or metabolic activity is retained during storage of the tissue or organ. In such embodiments, it is also desirable that the explanted tissue or organ retains at least about 95%, at least about 96%, at least about 97%, at least about 98% or even at least about 99% or more of at least one of the following parameters after storage in one of the disclosed viability-preserving storage compositions for an extended period of time: (a) pre- or immediately post-harvest cellular viability, (b) pre- or immediately post-harvest tissue integrity, (c) pre- or immediately post-harvest biochemical function; and/or (d) pre- or immediately post-harvest implantation compatibility or suitability.

In various applications of the present invention, it may be desirable to maintain a population of animal cells, or explanted mammalian tissues and/or organs for substantially longer periods, and particularly longer periods than are currently afforded by tissue storage and transport solutions previously existing in the art. In such instances of long-term storage, it is desirable that the viability of the stored biological samples remains at least about 60% or greater, and that the structural integrity and cellular function of the explanted biological material remains suitable for transplantation following such extended periods of storage. In such instances, it may often be desirable to store samples for periods of several days to several weeks or longer, without losing significant tissue viability.

In such instances, it is preferable that no more than about 20-35% of the pre-harvest viability is lost during the storage process, and preferably, no more than about 10% to 20% of the original tissue viability is lost upon extended storage. Likewise, in certain instances, it may be desirable to store the explanted biological material for periods of from several days to several weeks with no more than a 5 to 10% loss of original tissue viability during the storage period.

Similarly, it may also be desired in the practice of one or more of the disclosed methods to provide populations of cells or explanted tissue or organs that remain viable (e.g., at least 70%, 80%, or 90% or even greater viability) after periods of time of from about 1 day to about 1 week. Alternatively, it may be desirable to maintain significant viability of explanted tissues or organs (e.g., at least about 60%, 70%, or even 80% or greater viability) following periods of storage of from about 1 week to about 1 month, or even at least about two months or longer, depending upon the particular tissue or organ, and depending upon the particular composition formulated for a given application.

4.9 Use, Handling, and Storage of Preservation Solutions

It is also contemplated that the compositions of the present invention may be used not only as a storage or transport buffer, but may also be formulated as a wash solution or to bathe and cleanse tissues and organs that are either intracorporeal or extracorporeal, immediately prior to, or subsequently following donor explantation and/or recipient implantation. Such formulations may also be used as an irrigation solution to rinse newly harvested tissues or organs prior to storage in a subsequent buffer or storage solution. Similarly, the disclosed compositions may be employed in "one-time" fashion (i.e., the tissue or organ to be stored is first contacted, and then subsequently maintained within a single quantity of the composition). Alternatively, two or more discreet quantities (aliquots) of the tissue preservation composition may be sequentially contacted with the biological material in a series of steps (commonly referred to as "wash steps"), after which the desired tissues or organs is placed in a quantity of the "fresh" composition for subsequent storage and/or transport.

The compositions disclosed herein may be used to perfuse the tissues, organs, or circulatory system of the donor animal prior to harvest (either while the animal is still alive, or alternatively, postmortem). The disclosed compositions may also be used as a wash solution to cleanse the freshly-harvested tissues from the host animal prior to long-term storage, transport, or transplantation.

The tissue or organ may remain within the final quantity of storage solution substantially until implantation in the recipient host (for example during transport, or tissue banking), or alternatively, the tissue or organ may be serially transferred to, or sequentially washed in, multiple quantities of fresh storage solution at various times prior to, during, or subsequent to, tissue transport and/or banking. Likewise, the tissue or organ may be stored in a suitable container means or medical device that permits the continuous or discontinuous transfer of fresh storage solution into the container means or a device that sequentially replaces the "spent" storage fluid with "fresh" medium.

Such container means may employ one or more infusion, irrigation, or peristaltic pumps, for example, to facilitate the continuous or discontinuous transfer of storage medium to the biological material. Regardless of the particular quantity of the storage solution employed, or the frequency of which the storage medium is removed and replenished, standard laboratory precaution should be taken with respect to maintaining the sterility of the solution, minimizing fouling of the biological material, and preventing microbial, chemical, or enzymatic contamination of the biological tissue, or the storage solution itself. Such methodologies are within the knowledge of the skilled artisan in the field of clinical laboratory medicine, and tissue or organ transplantation, and as such, have been omitted for brevity's sake.

The compositions of the present invention are also not limited to any particular osmolarity/osmolality or pH; however, the skilled artisan will appreciate the need for employing compositions that are within the conventionally-accepted norms for storage and maintenance of living biological cells, tissues, or organs in general, and particularly within the conventionally-accepted norms for the storage and preservation of cellular activity of mammalian cells, tissues, and organs in particular.

As an illustrative example, the osmolality of the disclosed compositions will preferably be within a range of from between about 1 and about 10,000 mOsm/kg; more preferably in the range of from between about 10 and about 1,000 mOsm/kg; and more preferably still, in the range of from between about 100 and about 500 mOsm/kg.

Likewise, while the concentration of hydrogen ions (expressed as pH) in the disclosed compositions is not per se limited to any exact pH, the solutions employed in the context of the invention will preferably be within a pH range that is suitable and conducive to the maintenance of biological cells, tissues, or organs. As such, the inventors contemplate that the pH of the disclosed compositions will preferably be within the range of from between about pH 5.0 and about pH 9.0, more preferably in the range of from between about pH 5.5 and about pH 8.5, and more preferably still, in the range of from between about pH 6.0 and about pH 8.0.

Dissolved gas partial pressures may be approximately about 5 to 800 mm Hg, more particularly approximately about 10 to 600 mm Hg, and in some embodiments, the partial pressure of dissolved gases may be in the range of from about 50 to about 400 mm Hg. Exemplary dissolved gases may include, but are not limited to, ambient air, nitrogen, oxygen, carbon dioxide, or an inert gas such as argon, or combinations of one or more such gases. Similarly, the headspace above preservative solutions, in which biological cells or tissues are stored, may also comprise any suitable gas, or combination of gases, including, but not limited to, air, $O_2$, $N_2$, $CO_2$, or Ar.

In the practice of the present invention, it is often desirable to maintain the cells, tissues, or organs in the composition essentially from a time immediately post-harvest until the explant material is readied for transplantation into a recipient mammal. During the interval between harvest and implantation, it is also desirable to monitor and control the environmental conditions, and storage parameters to maintain the integrity, viability, and biochemical activity of the harvested biological material.

Preferably, by using the compositions described herein, a population of mammalian cells or a selected mammalian tissue or organ may remain substantially viable, and as such, retain substantial biologic activity, while stored in, and/or transported in, such a composition, for periods that are significantly longer than those afforded by either commercially-available buffers, or biological storage and/or organ and tissue transport/explantation storage solutions found in the prior art.

While it is contemplated that the parameters of storage temperature, atmospheric pressure, ambient environmental conditions, and such like will preferably be controlled to maximize the viability of the biological material, and to minimize the chance of contamination, or fouling of the tissue, the routine procedures known to those of skill in the art concerning tissue manipulation, organ harvest, tissue preparation, specimen handling, and controlling sterility and suitability of the environmental conditions under which the explanted tissue is stored and maintained prior to transplantation, have been omitted from the instant text for brevity's sake.

It is noted, however, that the compositions disclosed herein will find particular use in the storage and/or transport of tissues at an ambient storage temperature in the range of about −10° C. to about 25° C. (with the proviso that at least a portion of the storage solution preferably remain substantially in an un-frozen, or liquid state). While it is contemplated that slight variation in temperature during the storage/transport process will not adversely affect the integrity, biological function, or cellular viability of the stored tissue or organ, it is preferable that the material be maintained and transported under environmental conditions of approximately −10° C. and about 25° C., or more preferably from between about −5° C. and about 20° C., or more preferably still, from between about 0° C. and about 15° C., or even more preferably still, from between about 0° C. and about 10° C. whenever possible.

In illustrative embodiments, it has been shown that viability of stored animal tissues (and in particular, explanted mammalian tissues) is greatly enhanced when the preparation is stored under conditions of standard refrigeration, such as for example, at a temperature of from about 1° C. to about 5° C. (corresponding generally to a conventional laboratory cold storage devices, commercial refrigerators, controlled temperature storage units, and such like.

To preserve the integrity and viability of the biological material to the best extent possible, the inventors also contemplate that it will be most desirable to contact freshly-harvested cells, tissues, or organs with the disclosed tissue viability-preserving formulations substantially immediately upon harvest, and to maintain the harvested cells, tissues, or organs in these formulations substantially until immediately prior to implantation. Pre-cooling of the composition to the desired storage temperature prior to contacting it with the harvested cells or tissues will often be desirable.

Likewise, during any periods of transporting the materials outside of a controlled refrigerated environment, it will also often be desirable to provide proper cooling/refrigeration of the sample during transport. This can be achieved by several means known in the art, including for example, maintaining the sample in a portable refrigeration unit, transporting the tissue in an insulated container, or packaging the biological sample with dry or wet ice to maintain the desired temperatures during transport.

In certain circumstances, it may also be desirable to irrigate, infuse, perfuse, or wash the harvested biological material with one or more portions of the compositions immediately upon removal from the living or cadaveric donor organism, and then to subsequently transfer the washed biological material to a fresh aliquot of the composition just prior to storage.

In some circumstances, depending upon the tissue type, and the length of storage, it may also be desirable to periodically decant the "spent" medium from the stored tissue, and to replenish the storage means with fresh medium. Likewise, it may also be desirable to perform one or more additional perfusion or wash steps after removing the tissue from storage, and immediately prior to implantation into the recipient animal.

For example, the compositions of the present invention have been shown to prolong the survivability of explanted mammalian cells and tissues for periods of at least about 7 days (i.e., at least about 1 week), at least about 14 days (i.e., at least about 2 weeks), at least about 21 days (i.e., at least about 3 weeks), at least about 28 days (i.e., at least about 4 weeks or longer; at least about 35 days (i.e., at least about 5 weeks or longer; at least about 42 days (i.e., at least about 6 weeks or longer. In the practice of the present invention, it has been shown that explanted mammalian tissues may be stored under refrigeration conditions substantially in at least a first tissue viability-enhancing buffer/storage solution for periods of several days to several weeks while maintaining substantial cellular viability, tissue integrity, and biological function, sufficient for explantation of the tissue into selected animal recipients.

4.10 Explanted Biological Cells, Tissues, and Organs

The present invention also provides a population of cells, an explanted biological tissue or a harvested organ that is prepared by any one of the methods and processes described herein. Although there is no inherent limitations to the cell, tissue, or organ types that may benefit from being maintained and/or transported in one or more of the disclosed storage compositions, the inventors contemplate that in most circumstances, the explanted population of donor cells, tissue(s), or organ(s) to be maintained will generally be of animal origin, and in particular, of mammalian origin. Exemplary donor cell, tissues, and organs include, but are not limited to, those of human, bovine, ovine, porcine, equine, canine, feline, caprine, luprine, or non-human primate origin. In certain embodiments, the human may be a patient under the care of a physician or other medical professional, and is, will, or may have been in need of transplantation or one or more cells, tissues, or organs harvested from a suitable donor mammal.

Similarly, in most applications of the present methods, the recipient animals will preferably be mammalian species, such as livestock, animals under veterinary care, and most often, humans. Particularly desirable donor animals include, but are not limited to, those mammals from which cells, tissues, or organs may be harvested that are suitable for transplantation into a human recipient. These may include, but are not limited to cows, dogs, goats; horses, cats, chickens, humans, rabbits, hares, wolves, mice, rats, sheep, pigs, foxes, non-human primates, or other mammalian species from which tissues or organs may be harvested.

Likewise, while the inventors contemplate that almost any type of animal cells or tissues may be maintained in the disclosed storage compositions, in most circumstances, the cells and tissues will be of mammalian origin. Exemplary animal cells include, but are not limited to, one ore more cells selected from the group consisting of chondral, cartilagenous, osteochondral, islet, osteogenic, neural, bone, bone marrow, muscle, adult or embryonic stem cells, nucleus pulposus, cardiac cells, adipose cells, and skin. Exemplary mammalian tissues include, but are also not limited to, one or more mammalian tissues selected from the group consisting of bone, bone marrow, cartilage (including, for example, stratified, or non-stratified tissue-engineered porcine cartilage), tendon, ligament, vertebral disc, functional spine unit, corneas, lens, and other ocular tissues, blood vessels, heart valves, meniscus, hair, lung tissue, tooth and dental tissues, striated muscle, smooth muscle, cardiac muscle, adipose tissue, skin, fibrous tissue, neural tissue, connective tissue, cultured cell monolayers, muscle-tendon grafts, TECs, TEDs, and TEPs, in vitro or in situ, cell or tissue cultures, in situ or ex vivo biological grafts, in vitro or in vivo bioreactor products, allograft or autograft tissues, as well as muscle-tendon grafts and such like. Exemplary mammalian organs suitable for donor harvest and recipient transplantation include, but are not limited to, organs selected from the group consisting of cochlea, eye, heart, intestines, kidney, liver, lung, ovary, pancreas, skin, spleen, stomach, and testis.

4.11 Preservation Formulations Comprising Glucosamine, Chondroitin, and Related Compounds In exemplary embodiments, the invention also provides compositions that comprise, consist essentially of, or consist of (a) a biological buffer; growth medium, or organ transport solution; and (b) at least one cellular viability- or function-enhancing compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine, wherein the cellular viability- or function-enhancing compound is present in the composition in an amount effective to prolong the viability of a mammalian tissue, organ, or population of cells that are maintained in the composition under suitable environmental conditions, when compared to the maintenance of such tissue, organ, or population of cells stored in the biological buffer, growth medium, or organ transport solution alone. Preferably the cellular viability-enhancing compound(s) is/are present in the composition at a final concentration of between about 0.0001% and about 1% (vol./vol.), or more preferably, of between about 0.001% (vol./vol.) and about 0.10% (vol./vol.).

Likewise, the present invention also provides a tissue storage/transport solution that comprises, consists essentially of, or, alternatively, consists of (a) a biological buffer; growth medium, or organ transport solution; (b) at least one cellular viability-enhancing compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine; and (c) at least one biomembrane sealing agent, wherein the biomembrane sealing agent and cellular viability-enhancing compound are each present in the composition in an amount effective to prolong the viability of a mammalian tissue, organ, or population of cells that are maintained in the composition under suitable environmental conditions, when compared to the maintenance of such tissue, organ, or population of cells stored in the biological buffer, growth medium, or organ transport solution alone.

Similarly, the invention also provides a tissue storage/transport solution that comprises, consists essentially of, or, alternatively, consists of: (a) a biological buffer; growth medium, or organ transport solution; (b) at least one cellular viability-enhancing compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetyl glucosamine; (c) at least one biomembrane sealing agent; and (d) at least one chelator; wherein the biomembrane sealing agent, chelator, and cellular viability-enhancing compound are each present in the composition in an amount effective to prolong the viability of a mammalian tissue, organ, or population of cells that are maintained in the composition under suitable environmental conditions, when compared to the maintenance of such tissue, organ, or population of cells stored in the biological buffer, growth medium, or organ transport solution alone.

In another embodiment, the present invention also provides a tissue storage/transport solution that comprises, consists essentially of, or, alternatively, consists of: (a) a biological buffer; growth medium, or organ transport solution; (b) at least one cellular viability-enhancing compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine; (c) at least one biomembrane sealing agent; (d) at least one chelator; and (e) at least one antioxidant; wherein the cellular viability-enhancing compound, biomembrane sealing agent, chelator; and antioxidant are each present in the composition in an amount effective to prolong the viability of a mammalian tissue, organ, or population of cells that are maintained in the composition under suitable environmental conditions, when compared to the maintenance of such tissue, organ, or population of cells stored in the biological buffer, growth medium, or organ transport solution alone.

In illustrative embodiments exemplary cellular viability-enhancing compounds include, but are not limited to, compounds selected from the group consisting of chondroitin, chondroitin sulfate, glucosamine, glucosamine hydrochloride, and glucosamine sulfate.

4.12 Cellular/Tissue Viability Determination Assays

Although the viability of cells, tissues, and organs, and particularly those obtained from animals, can be determined by a number of published assays that are known to those of skill in the relevant art, in the present invention, the viability of cells is readily determined by using a microscopic assay that is commonly referred to in the art as a "live/dead assay" (Huntley et al., 2005). In one such assay, the biologic dyes 5-chloromethylfluorescein diacetate and propidium iodide (which differentially stain living and non-living cells) are employed and evaluated by a microscopy-based assay. Such dyes are typically fluorescent, and the fluorescence may be detected and used to produce dual-parameter fluorescence histograms, most typically using fluoromicroscopic techniques to distinguish the living vs. the non-living cells, in which the living and non-living cells each fluoresce at distinctly-different wavelengths.

To determine the % viability of tissues that have been stored as a function of time, a biological sample may be initially assayed for viability (typically within 48 hours of harvest from the donor animal) to determine an "initial viability." Subsequent viability determinations are then made on the tissue over a period of time to determine "current viability." The % viability can therefore be determined at any time post-harvest using the following equation:

[(current viability)/(initial viability)]×100=Percent viability

If desired, multiple samples may be analyzed and averaged both at initial assay, and/or during subsequent analyses to determine an "average viability" of the harvested tissue.

In addition to the live/dead cell staining described herein, the viability of cells, tissues, or organs may be determined by one or more of a variety of well-known biological viability assays, including for example, by quantitation of $^{35}SO_4$-uptake (Pennock et al., 2006), or by glycosaminoglycan (GAG) quantitation (Pennock et al., 2006) to name only a few.

Alternatively, the determination of tissue, cell, or organ viability may also include one or more biochemical or anatomical assays that are known in the art, and which provide qualitative and/or quantitation evidence of the biological activity or functionality of the explanted tissue once it is introduced into the recipient animal.

4.13 Cryogenic Preservation of Mammalian Tissues

In the practice of any of the disclosed methods of the present invention, the methods may also optionally comprise one or more additional steps. For example, under certain circumstances, it may be desirably to optionally provide a step of cryogenically-preserving (i.e., freezing) a population of cells, tissues, or organs using one of the disclosed tissue preservative buffers, solutions, or supplemented growth media.

In such methods, the step of freezing the tissue or cell sample may optionally include the addition of one or more cryoprotectants or cryopreservative compounds to further permit freezing of the sample, and/or maintenance of the sample at temperatures generally below 0° C. Exemplary cryoprotectants and/or cryopreservative compounds, as used in the context of the present invention may include, but are not limited to, ice-suppressing cryoprotectants (e.g., non-colligative agents such as Supercool X-1000™ and Supercool Z-1000™, 21$^{st}$ Century Medicine, Rancho Cucamonga, Calif.) glycerol, dimethylsulfoxide (DMSO), ethylene glycol, propylene glycol, polyethylene oxide (PEO), acetamide, ethanol, methanol, butanediol, carbohydrates (including sugars such as glucose, fructose, dextrans, sucrose, lactose, and trehalose), polyvinyl alcohols, hydroxyethyl starch, serum albumin, and such like.

Likewise, in the practice of the disclosed methods, it may also be desirable to provide one or more optional additional steps in method, including, for example, steps that involve freezing and/or thawing of a tissue sample or cell population. Such freezing and thawing steps may be achieved by any conventional manner known to those in the art, (e.g., slowly bringing the temperature of a refrigerated tissue or cell sample down to a suitable sub-zero temperature, or alternatively, slowly bringing the temperature of a sub-zero stored sample up to refrigerated (and, optionally, to either room or recipient body temperature immediately prior to implantation). Such additional steps in the method may employ submersion vessels or frozen storage means to prepare the frozen tissue or cell sample, while conventional means such as a heated water bath or such like device, submerging the frozen sample directly into a sample of growth medium, biological buffer, or tissue/organ storage solution (e.g., pre-warmed to the desired temperature), may be employed to bring the temperature of a frozen tissue sample to the desired temperature required for transplanting the biological material into the body of a suitable recipient animal.

4.14 Commercial Formulations and Kits

The present invention also provides kits and other commercial-ready adaptations of the disclosed compositions to facilitate preparation of working formulations of the final tissue storage/preservation medium.

For example, such kits may comprise, in suitable container means, a stock solution of comprising a tissue viability-prolonging composition, in combination with a commercially-available buffer, growth medium, diluent, or storage solution. Such kits may comprise any convenient amount of such components, and the components may even be pre-measured such that the entire contents of the stock solution is added to the entire amount of storage medium solution in the kit to produce a one-step, or "ready-to use" final working solution obtained simply by combining the two pre-measured amounts. For example, a quantity of storage medium may be pre-measured and aliquotted into a suitable storage receptacle, and a pre-measured amount of the medium supplement (e.g., a biomembrane sealing agent+an antioxidant+an iron chelator) may be provided with the medium in a separate sterile ampoule. Using aseptic techniques, the pre-measured quantity of medium supplement may then be added to a standard growth medium or buffer, to provide a ready-to-use formulation to which the biological tissue is subsequently added.

Alternatively, a kit may be provided with excess quantity of one or more of the active ingredients, or one or more storage media, buffer, etc. Instructions for using the compositions, or a protocol for storage and/or transport of particular type(s) of biological material(s) may also optionally be provided within the kit to instruct one of skill in the art in the use of the kit, or how to prepare the precise amounts of each reagent to provide the desired preservation a solution that comprises the active ingredients of the compositions.

To facilitate timely and accurate combination of the ingredients, the kits may also provide means for combining two or more ingredients, such as for example, a sterile syringe or other suitable sterile delivery means for adding a smaller quantity of one solution into a larger quantity of a second solution (e.g., a concentrated form of the supplement may be prepared in a sterile delivery means, which is then used to introduce a quantity of the supplement to a separate container of standard commercially-available growth medium or buffer solution to form the final working compositions as disclosed herein.

In other embodiments, the kits of the present invention may further optionally comprise one or more instruction(s) or protocol(s) detailing the recommended use of the disclosed compositions as a rinse solution prior to, during, or subsequent to the harvesting, storage, handling, and/or transportation of the biological material using one or more of the disclosed compositions.

The kits of the present invention may also optionally include one or more containers for storing the biological sample, or one or more devices for obtaining, explanting, or implanting the biological material into a suitable recipient. Such kits may also be prepared for convenient commercial packaging, sale, use, and transport. Exemplary packaging means for harvest, storage, and/or delivery of the biological material include, but are not limited to, gas-permeable or gas-impermeable containers, with or without a gaseous headspace. Such packaging means may incorporate the use of clear or opaque plastics, as well as hard, or flexible packaging. The standard methods for collecting, preparing, storing, and transporting explanted biological materials are considered to be within the purview of the artisan skilled in the transplantation arts, and as such, are not described in further detail herein.

In certain embodiments, the compositions and kits of the present invention, as well as one or more biological samples stored therein, may also be useful in the prophylaxis, therapy, or amelioration of symptoms of one or more diseases, dysfunctions, defects, injuries, or disorders in a mammal. Such compositions may also find particular use in the preparation of a medicament for prophylactic, therapeutic, and/or ameliorative regimens, particularly in the harvesting of biological materials from donor animals, or in the surgical transplantation of such materials into selected recipients.

4.15 Exemplary Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of clarity, the following specific terms are defined below:

As used herein, the terms "patient" and "recipient" are intended to include animals, and in particular, mammalian species such as human beings, livestock, or animals under veterinary care and/or supervision.

As used herein, an "antioxidant" is a substance that, when present in a mixture or composition that comprises one or more oxidizable substrates, delays, retards, or substantially prevents oxidation of the substrate in the mixture or composition.

As used herein, a "chelator" or "chelating agent" is a substance that, when present in a mixture or composition that comprises one or more metal or metal ions, binds, inactivates, or substantially reduces the concentration of free metal or free metal ions in solution.

As used herein, the terms "autograft" and "autologous graft" are coextensive, and are used to mean a population of cells, tissues, or an organ that is explanted harvested) from a body site of a host mammal and subsequently reimplanted into the same mammal from which it was obtained. Examples of autografting include inter alia the implanting of healthy skin from one part of a patient's body to another part of the body where, for example, the native skin has been burned or damaged. Another example involves the autogenic grafting of osteochondral/bone tissues removed from one site on a patient's body, and used to mediate an osteoinsufficiency by implantation at another site in the same patient's body.

Likewise, as used herein, the terms "allograft" and "allogenic graft" are coextensive terms which are used to describe a population of cells, tissues, or an organ that is explanted (harvested) from one donor animal and transplanted into another genetically non-identical recipient animal of the same species.

As used herein, the terms "isograft" and "isogenic graft" are coextensive terms, which are used to describe the transplantation of a population of cells, tissues, or an organ from a suitable donor animal into the body of its genetically-identical sibling (i.e., a twin).

In addition, as used herein, the terms "xenograft" and "xenogenic graft" are coextensive terms that are used to describe the transplantation of a population of cells, tissues, or an organ from a suitable donor animal of one species into the body of a suitable recipient animal of another species. Exemplary xenografts include, but are not limited to, the transplantation of porcine (pig) tissues into a recipient human.

The terms "biological sample(s)" and "biological material(s) are used interchangeably herein, and are intended in an overall broad sense to encompass any sample or material that is obtained from a biological entity, or any population of cells and/or tissues that are of biological origin. Such sources include, without limitation, whole or dissected tissues, including cells, tissues or organs obtained from biopsy, autopsy, and/or necropsy, as well as aspirates or lavages; in situ or in vitro cells (including, e.g., individual cell, populations of cells, confluent or monolayer cells, or cell populations, transformed cell lines, tissue and/or cellular explants, TECs, TEDs, TEPs, in vivo, in vitro, in situ, ex situ, and ex vivo biological grafts, allografts, autografts, isografts, xenografts, autologous graft tissues, as well as muscle-tendon grafts, structural spine units, and such like.

The terms "medium, "media," "biological medium," and "biological media" are used throughout the Specification in a broad sense, and are intended to encompass a variety of solutions, buffers, formulations, and/or compounds, in which a specific biological organism, cell, tissue, organ, or other type of biological samples or materials may reside for any period, of time that is conducive to the preservation of viability of the biological material placed within such buffers, solutions, formulations, and/or compounds.

The term "buffer," as used herein, refers to aqueous solutions or compositions that resist changes in pH when acids or bases are added to the solution. Solutions that exhibit buffering activity are often referred to in the art as "buffers" or "buffer solutions." Buffers typically are able to maintain the pH of the solution within defined ranges, often for example between pH 5.5 and pH 7.5. Buffer solutions that are typically able to maintain a pH of approximately 7, are often referred to a "physiological buffers." Exemplary biological buffers include, but are not limited to, Lactated Ringer's solution, physiological saline solution, N-(2-Acetamido)-2-aminoethanesulfonic acid (ACES); N-2-acetamido-2-iminodiacetic acid (ADA); N,N-bis(2-hydroxyethyl)-2-aminoethanesulfonic acid (BES); N,N-bis(2-hydroxyethyl)glycine (BICINE); 2-bis(2-hydroxyethyl) amino-2-(hydroxymethyl)-1,3-propanediol (BIS-TRIS); 3-(cyclo hexylamino)-1-propanesulfonic acid (CAPS); 3-(cyclohexylamino)-2-hydroxy-1-propanesulfonic acid (CAPSO); 2-(cyclohexylamino) ethanesulfonic acid (CHES); (N,N-bis[2-hydroxyethyl]amino)-2-hydroxypropanesulfonic acid (DIPSO); 4-(2-Hydroxyethyl)-1-piperazinepropanesulfonic acid (EPPS); 4-(2-hydroxyethyl) piperazine-1-ethanesulfonic acid (HEPES); 4-(2-hydroxyethyl) piperazine-1-(2-hydroxypropane sulfonic acid) (HEPPSO); 2-(N-morphilino)ethanesulfonic acid (MES); 3-(N-morpholino)propanesulfonic acid (MOPS); 3-morpholino-2-hydroxypropanesulfonic acid (MOPSO); piperazine-1,4-bis(2-ethanesulfonic acid) (PIPES); piperazine-N,N'-bis(2-hydroxypropane sulfonic acid) (POPSO); [(2-hydroxy-1,1-bis(hydroxy methyl)ethyl)amino]-1-propanesulfonic acid (TAPS); 3-(N-tris[hydroxymethyl]methylamino)-2-hydroxypropanesulfonic acid (TAPSO); 2-[(2-hydroxy-1,1-bis (hydroxylmethyl)ethyl)amino]ethanesulfonic acid (TES); N-[tris(hydroxymethyl)methyl]glycine (TRICINE); and tris (hydroxymethyl)amino methane) (TRIS); mixtures or derivatives thereof, as well as other biological buffers including those developed by Good et al. (1966).

The terms "donor tissue," "excised tissue" and "harvested tissue" are intended to describe tissues that were removed from the body of a living or deceased (cadaveric) animal donor.

The terms "donor cells," "harvested cells" and "population of cells" are intended to describe one or more biological cells or pluralities of biological ells that either are obtained from the body of a living or cadaveric animal donor, or alternatively, are obtained from the in vitro or in vivo culturing of a population of such cells.

The terms "donor organ," "explanted organ" and "harvested organ" are used herein to describe one or more organs that are obtained from the body of a living or cadaveric animal donor.

The terms "viable cell(s)," "viable tissue(s)," and "viable organ(s)" in the context of the present invention mean (as contextually required) one or more cells, tissues, and/or organs, respectively, that comprise at least a first population of living cells that are capable of surviving and substantially maintaining their extant biological function provided that they are harvested, stored, maintained, cultured, transported, and/or transplanted under the necessary biological conditions (e.g., nutrients, incubation temperature, etc.) effective to maintain the viability of such cells, tissues or organs sufficient for implantation into a suitable recipient host.

While the inventors have expressed exemplary formulations using a % volume/volume (vol./vol.) basis throughout the Specification, calculation of the final working concentration of a selected compound (as well as determination of any concentrated "stock" solutions that may subsequently be diluted to achieve the final "working" solution) need not be limited to a % vol./vol. basis. For example, it may be particularly facile to utilize a % weight/volume basis for preparing a solution to which a solid or powder form is added. Likewise, in certain embodiments (e.g., where the viscosity or density of a given compound makes accurate volumetric determinations impractical, one may formulate the disclosed compositions on a wt./wt. percentage basis. Such equivalencies are all intended to fall within the scope of the present teaching.

Likewise, all integers and sub-ranges within a given range of measurement (e.g., concentration) are also specifically considered to fall within the scope of the present teaching. For example, where a particular range of concentration is given, for example, "between about 0.001% and about 50%" or "from about 0.001% to about 50%" or "within the range of from 0.001% to 50%," etc., it is specifically intended that all intermediate sub-ranges (e.g., "from 0.01% to 40%", or "from 0.02% to 20%" etc.) are explicitly included within the scope of the present invention. Likewise, all intermediate integers within a stated concentration range or sub-range are also explicitly encompassed by the present teaching. Therefore, it is understood that recitation of a concentration that falls within the range of "between about 0.001% and about 50%" (inter alia, e.g., 0.01%, 0.1%, 1.0%, 2%, 10%, 23%, 31.5%, 42.15%, 48.99%, etc.) implicitly fall within the scope of the present teaching and the subject matter claimed herein. Likewise, the present specification encompasses both open-ended (e.g., "at least 1%," "at least 1.5%," "less than about 2%," "not more than 5 percent" etc.), as well as all closed-ended sub-ranges within a stated numerical range (e.g., the sub-ranges "between about 0.01% and about 20%" or "between about 0.01% and about 33%," or "from approximately 0.01% to approximately 40%," each implicitly falls within the numerical range "from about 0.01% to about 50%."

In the context of the invention, the term "about" is given its ordinary meaning of "approximately." Thus, the term "about 1 week" is intended to mean a period of time of approximately 7 days (equivalent to "approximately 168 hours"), which may, of course, be slightly longer than, or slightly shorter than the exact stated numerical amount. Likewise, the phrase "at least about X days" may be used to describe an interval of time that is "approximately," "nearly," or "almost" 'X' days in length or duration, but which need not necessarily be "X" days exactly. Such a time interval may be slightly less or slightly more than the absolute numerical value of "X" itself. Such understanding of the terms about and approximately are within the general knowledge of the skilled artisan, and the foregoing example is provided only to illustrate the "flexibility" the adverbs "about" and/or "approximately" render to the nouns that they modify.

In the context of the invention, a period of "about 20-30 days" is understood to be inclusive of periods that are about 20 days, about 21 days, about 22 days, about 23 days, about 24 days, about 25 days, about 26 days, about 27 days, about 28 days, about 29 days, or about 30 days, and even is inclusive of periods that may be on the order of about 19 days, or even about 31 days, to and including the fractional intervals of time within the stated range(s).

In the context of the invention, a period of "about 30-40 days" is understood to be inclusive of periods that are about 30 days, about 31 days, about 32 days, about 33 days, about 34 days, about 35 days, about 36 days, about 37 days, about 38 days, about 39 days, or about 40 days. The term "about 30-40 days" is also implicitly inclusive of periods of time that may be about 28 or 29 days, or even about 41 or 42 days, to and including the fractional intervals of time within the stated range(s).

For purposes of clarity, it is noted similarly, that a period of time that is "at least 7 weeks" by definition encompasses periods that are approximately equal to, or greater than 7 weeks in duration. Similarly, a period that is "about 8 weeks" in duration, or "about nine weeks" in duration, necessarily falls within the scope of a time interval that is stated to be "at least 7 weeks" in length.

The term "appropriate conditions" is used to illustrate the normal conditions under which a given population of cells, tissues, and/or organs would be exposed that would facilitate viability and preserve biologic function of the given biological sample.

As used herein, the term "comprising" and its cognates are used in their inclusive sense; that is, equivalent to the term "including" and its corresponding cognates.

The articles "a," "an," and "the" explicitly include plural references unless the context clearly dictates otherwise.

5. BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The following drawings form part of the present specification and are included to further demonstrate certain aspects of the present invention. The invention may be better understood by reference to the following description taken in conjunction with the accompanying drawings, in which like reference numerals identify like elements, and in which:

FIG. 1 shows percent viability of porcine cartilage from intact osteochondral allografts stored at refrigeration temperatures (~2° C. to about 10° C.) as determined by live/dead fluorescent staining. Grafts were stored in a variety of standard commercially-available culture media (DMEM, RPMI, and EMEM). The average viability of porcine cartilage stored in all tested culture media was calculated and is also plotted.

Figure 2:
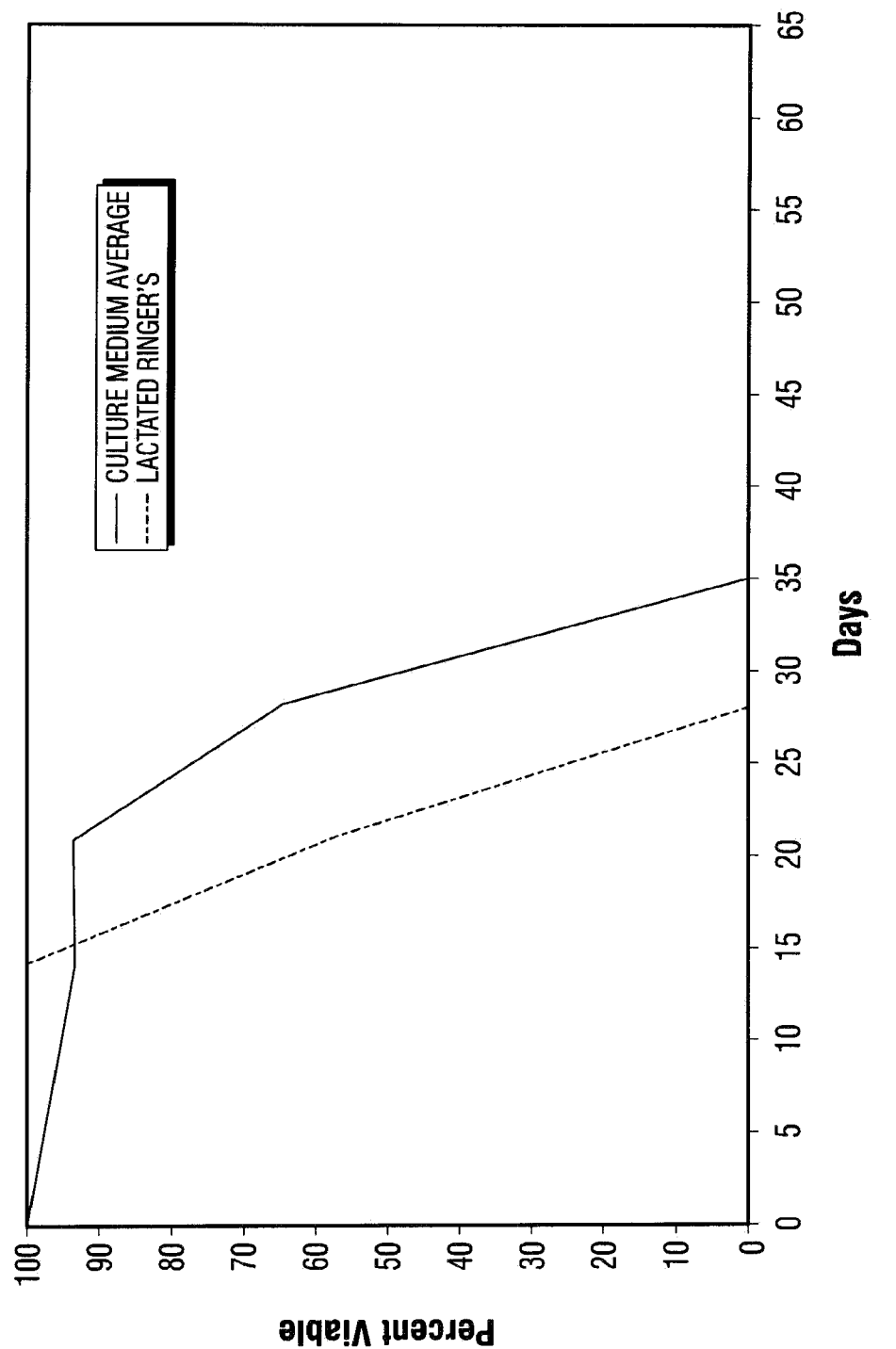

FIG. 2 shows the percent viability of porcine cartilage from intact osteochondral allografts stored in lactated Ringer's solution (Baxter, Deerfield, Ill.) or in an average culture medium at refrigerated temperatures (~2° C. to about 10° C.) as determined by live/dead fluorescent staining.

Figure 3:
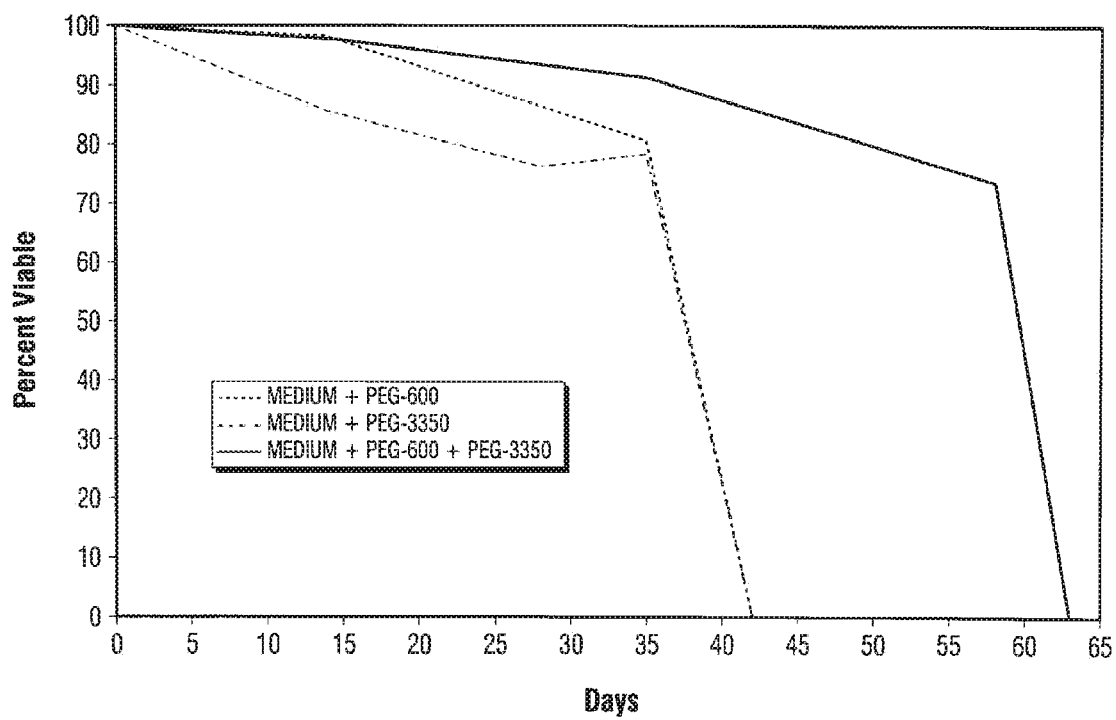

FIG. 3 shows the percent viability of porcine cartilage from intact osteochondral allografts stored in standard culture media at refrigeration temperatures (~2° C. to about 10° C.) as determined by live/dead fluorescent staining. These data demonstrate the addition of PEG (e.g., PEG-600 [a PEG polymer having an average MW≈600 Da], PEG-3350 [a PEG polymer having an average MW≈3350 Da], and PEG-600/3350 (alternatively expressed as "PEG-600+PEG-3350" [a combination of two PEG polymers, the first having an average MW of about 600 Da, and the second having an average MW of about 3350 Da]) to these media resulted in significantly improved viability of the tissue during long-term storage. In this study, PEG-600 was employed at a working concentration of 1.3% (vol./vol.), PEG-3350 was employed at a working concentration of 1.5% (wt./vol.), and the PEG-600+PEG-3350 combination (i.e., PEG-600/3350) was employed at a cumulative concentration of the two individual MW PEG polymers (e.g., PEG-600 1.3% [vol./vol.]) and PEG-3350 1.5% [wt./vol.]).

Figure 4:
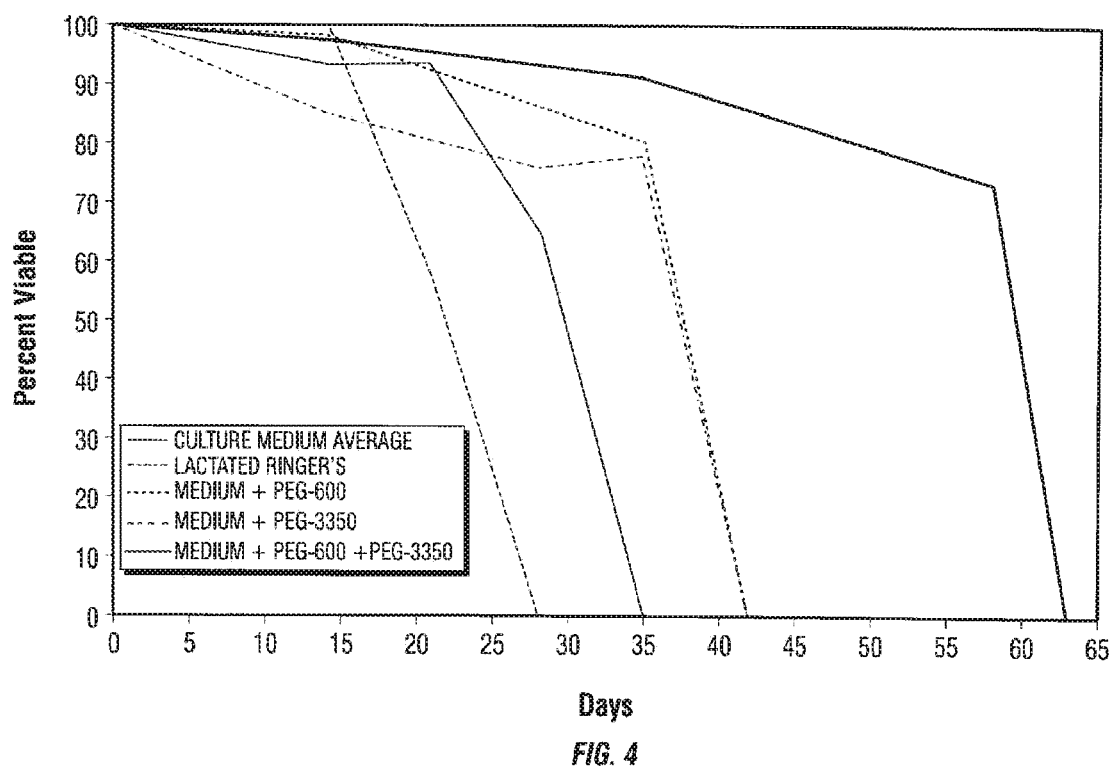

FIG. 4 shows the percent viability of porcine cartilage from intact osteochondral allografts stored in PEG-supplemented standard culture medium at refrigeration temperature (~2° C. to about 10° C.) as determined by live/dead fluorescent staining. This is a combined graph of the results shown in FIG. 2 and FIG. 3 to illustrate the improvement in viability resulting from the addition of one or more PEG polymers to standard culture medium. Conditions and materials were the same as described in the legends to FIG. 1, FIG. 2, and FIG. 3.

Figure 5:
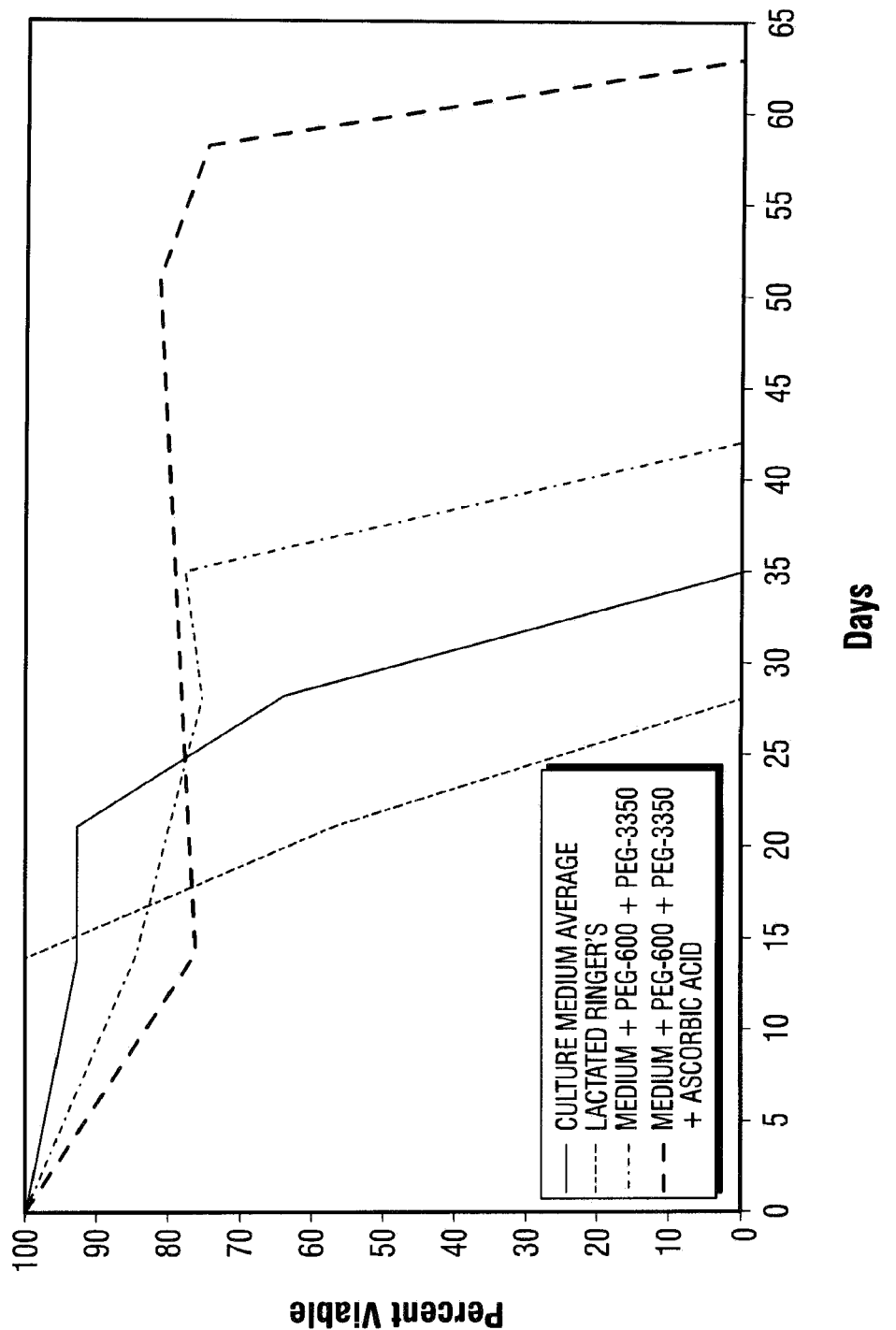

FIG. 5 shows the percent viability of porcine cartilage from intact osteochondral allografts stored at refrigeration temperature (~2° C. to about 10° C.) as determined by live/dead fluorescent staining. A graph showing the additive effects obtained when standard culture medium was supplemented with PEG-600, PEG-3350, and the antioxidant, ascorbic acid. Conditions and materials were the same as described in the legends to FIG. 1, FIG. 2, and FIG. 3.

Figure 6:
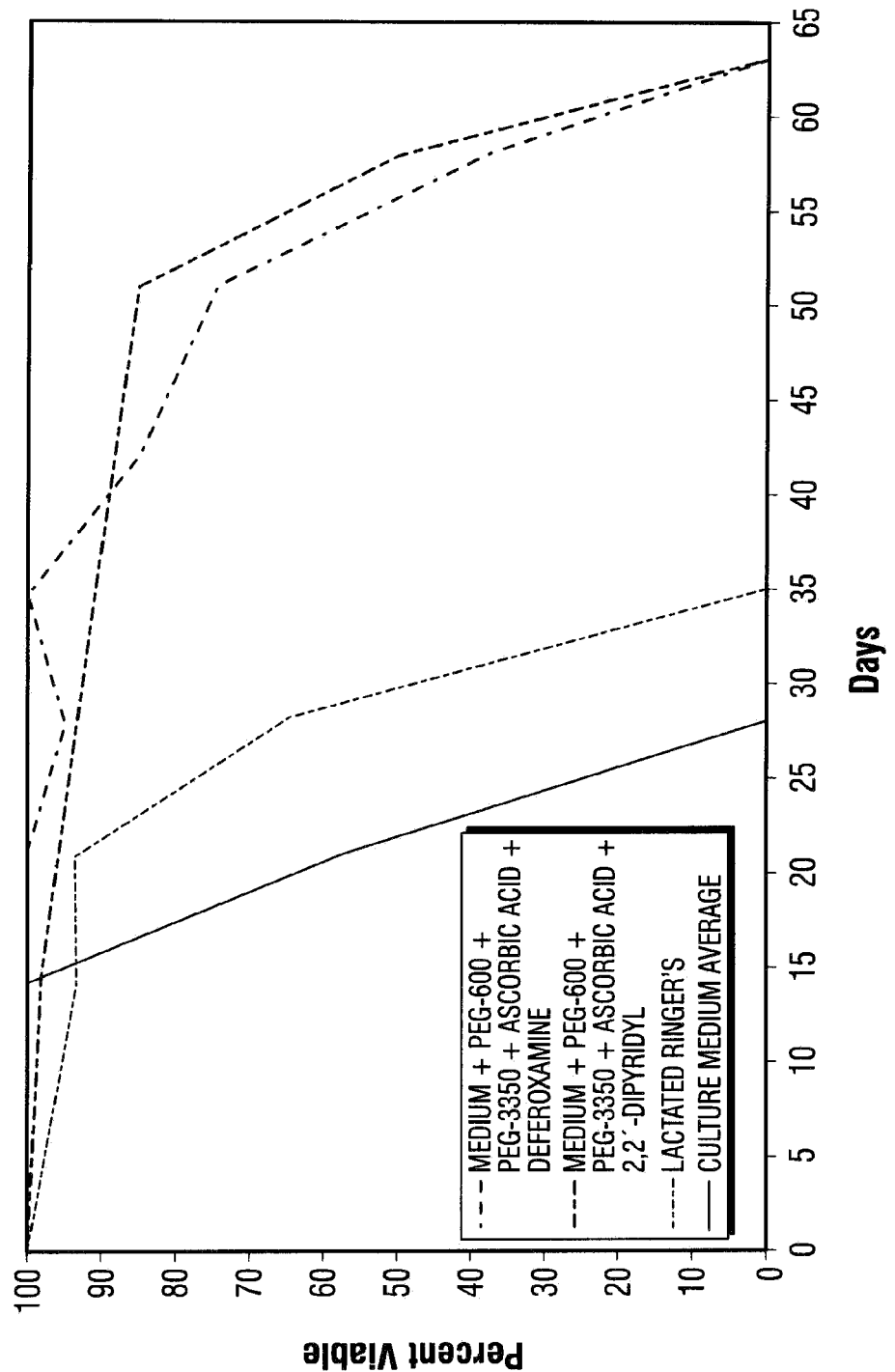

FIG. 6 shows the percent viability of porcine cartilage from intact osteochondral allografts stored at refrigeration temperature (~2° C. to about 10° C.) as determined by live/dead fluorescent staining. A graph showing the effect of culture medium supplemented with PEG-600/3350, ascorbic acid and either of the metal ion chelators deferoxamine mesylate or 2,2'-dipyridyl. These two data sets were then compared to either culture medium or lactated Ringer's solution alone. Conditions and materials were the same as described in the legends to FIG. 1, FIG. 2, and FIG. 3.

Figure 7:
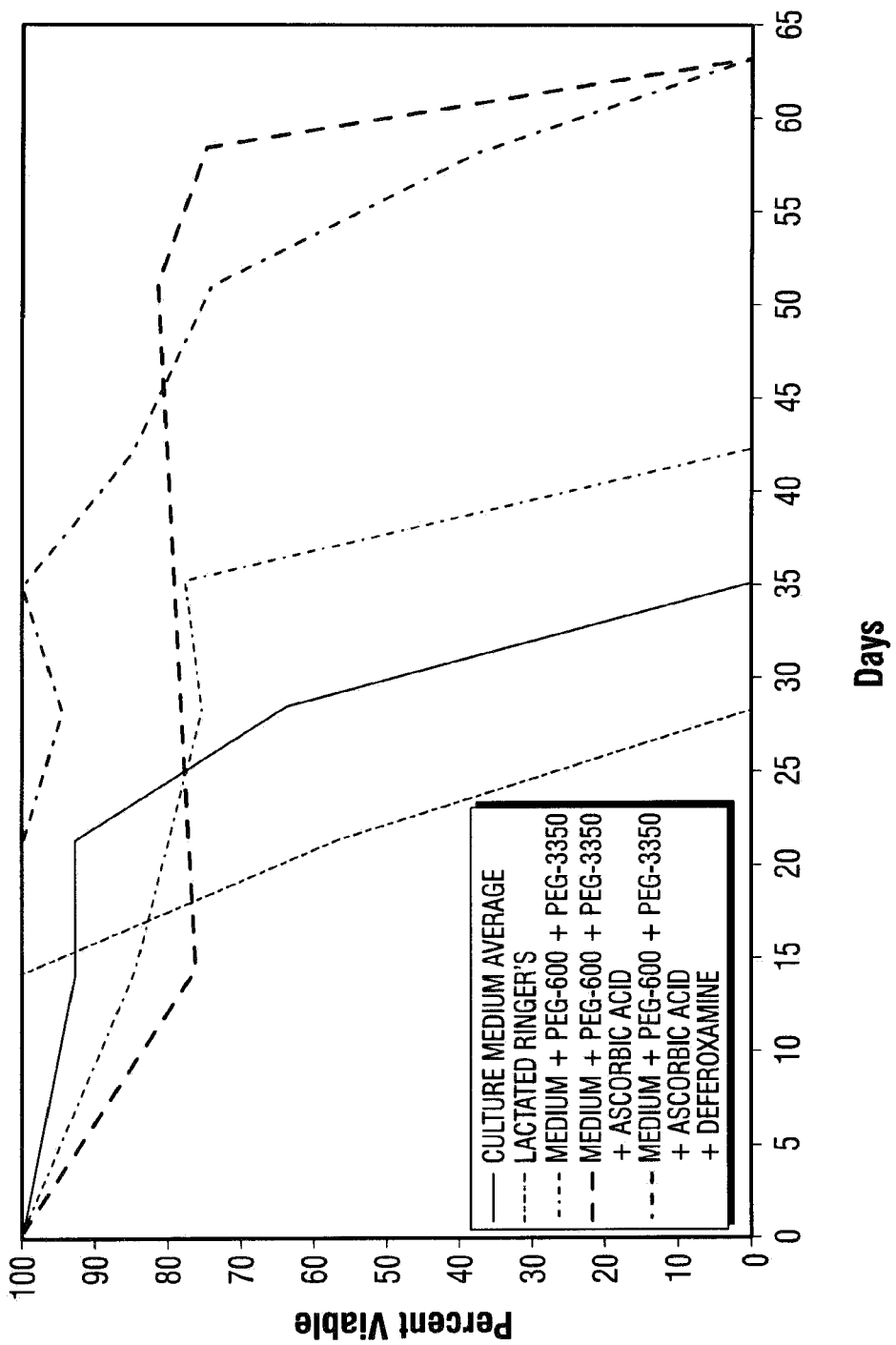

FIG. 7 shows the percent viability of porcine cartilage from intact osteochondral allografts stored at refrigeration temperature (~2° C. to about 10° C.) as determined by live/dead fluorescent staining. This figure shows a combination of data from previous figures and illustrates base-line viability provided by lactated Ringer's solution. Conditions and materials were the same as described in the legends to FIG. 1, FIG. 2, and FIG. 3.

Figure 8:
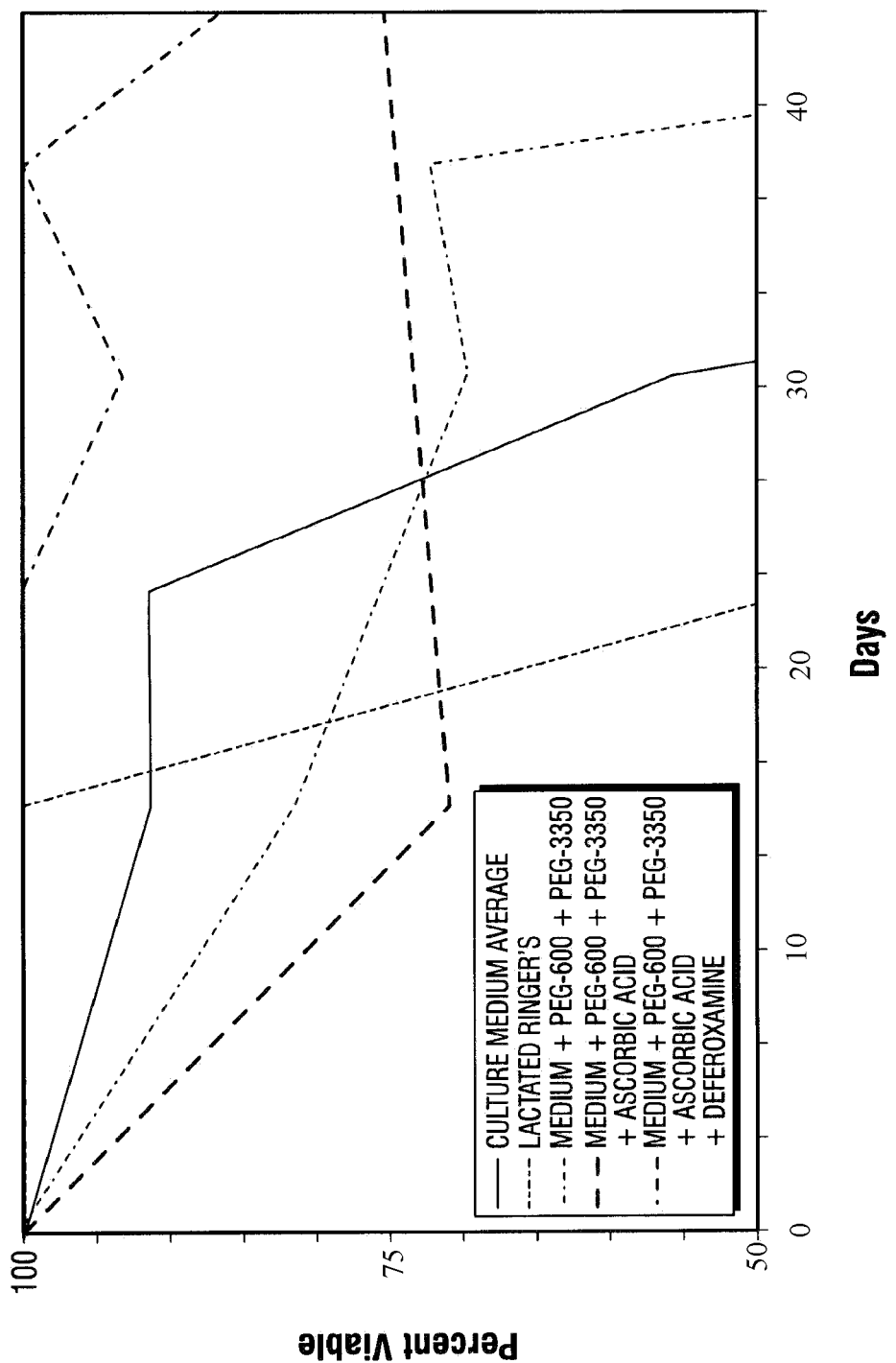

FIG. 8 shows the percent viability of porcine cartilage from intact osteochondral allografts stored at refrigeration temperature (~2° C. to about 10° C.) as determined by live/dead fluorescent staining. This figure contains the same data presented in FIG. 7, but illustrated with a change of scale to emphasize the short term improvement in viability of provided by disclosed preservative compositions. Conditions and materials were the same as described in the legends to FIG. 1, FIG. 2, and FIG. 3.

Figure 9:
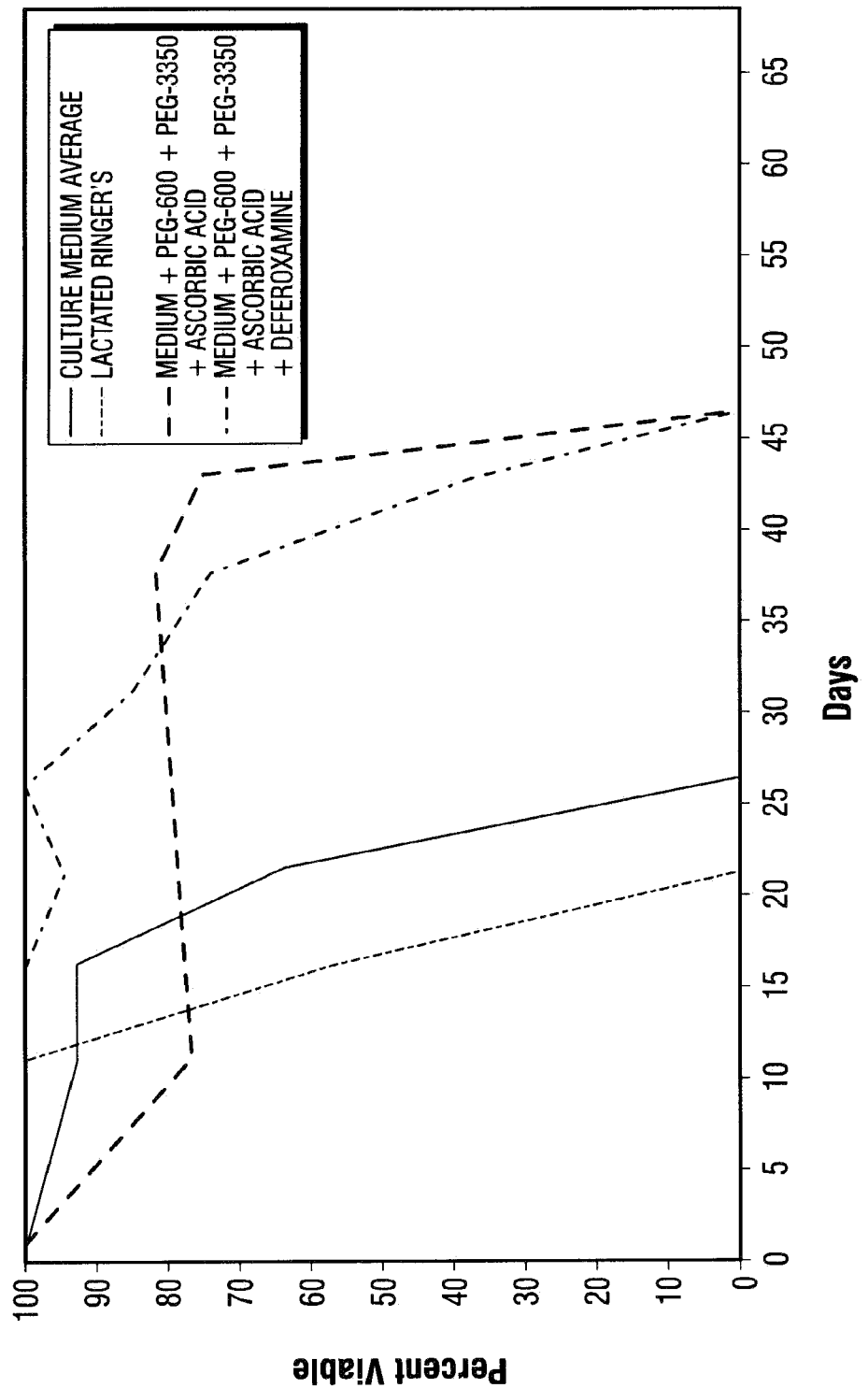

FIG. 9 shows the percent viability of porcine cartilage from intact osteochondral allografts stored at conventional refrigeration temperature (~2° C. to about 10° C.) as determined by live/dead fluorescent staining. Shown are the results of lactated Ringer's solution alone; culture medium alone; culture medium+PEG-600/3350+ascorbic acid; and culture medium+PEG-600/3350+ascorbic acid+deferoxamine. Conditions and materials were the same as described in the legends to FIG. 1, FIG. 2, and FIG. 3.

6. EXAMPLE—COMPARISON OF VIABILITY-PRESERVING PROPERTIES OF VARIOUS

Tissue Preservation-Enhancing Compositions

The following example is included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In these studies, the donor animal was sacrificed, and within 48 hrs of death, the tissues selected for explantation were removed for the donor and prepared for viability analysis and subsequent storage. At the time of packaging, several samples were assayed using live/dead fluoromicroscopic analyses to determine initial cell viability.

Four-mm diameter biopsy punches were used to harvest samples of the donor cartilage and bone, with multiple samples being analyzed and averaged to determine an average initial viability of the harvested tissue. All subsequent % viability calculations were based on this initial viability using the following equation:

$$[(\text{current viability})/(\text{initial viability})] \times 100 = \text{Percent viability}$$

Table 1 and Table 2 summarize results from comparison of the tissue viability-preserving properties of various conventional growth media, buffers, and the novel compositions of the present invention. These results track the percent viability of porcine cartilaginous tissue samples as a function of time (in seven-day increments from day 0 to day 91), and as a function of medium formulation. Shown are the percent viability determinations for porcine cartilage stored in lactated Ringer's solution alone, DMEM alone, EMEM alone, RPMI alone, AIM-V® alone, as compared to standard culture medium supplemented with PEG-600, PEG-3350, a combination of the two PEGs, and standard culture medium containing the combination of two distinct PEGs further supplemented with one or more antioxidant(s) (e.g., 2,6-di-tert-butyl-4-methylphenol or ascorbic acid), and one or more chelator(s) (e.g., deferoxamine mesylate, 2,2'-dipyridyl, or 1,10-phenanthroline). A portion of these data is illustrated graphically in the figures included herewith and described infra.

For example, in FIG. 1, one sees the results of a study that illustrates the percent viability of porcine cartilage from intact osteochondral allografts stored in a variety of standard commercially-available culture media (including e.g., DMEM, EMEM, AIM-V®, and RPMI), as well as storage in lactated Ringer's solution alone, as determined over time and under identical refrigerated storage conditions. This graph illustrates the average viability of the porcine cartilage stored in each of the different growth media. The curve representing a statistical average of the results of the four individual growth media alone is compared to additional results obtained in FIG. 2. In this study, all tissue samples were maintained under identical refrigeration temperatures (~2° C. to 10° C.), and the percent viability was determined for each time point using a standard live/dead fluoromicroscopic staining assay.

Turning to FIG. 2, the inventors have taken the curve from FIG. 1 showing the average of the four growth media tested, and compared the viability of porcine cartilage from intact osteochondral allografts stored in them to the viability of similar tissue stored only in lactated Ringer's solution. Again, the results suggest that at very short-term storage (<5 days or so), both standard culture medium and a conventional lactated Ringer's solution behave somewhat similarly with respect to the preservation of cellular viability of cartilage tissues stored in them. While 95% or greater viability was observed for tissues stored in either medium at day 15 of the study, beyond that time point, the tissues stored in lactated Ringer's solution quickly lose viability—by day 28 no living cells were detectable in the tissues maintained in Ringer's solution alone. In sharp contrast to these results, significant viability of tissues was observed in the aggregated growth media of FIG. 1 at day 25 (~90%), and even day 30 (~68%).

In this study, all tissue samples were maintained under identical refrigeration temperatures (~2° C. to 10° C.), and the percent viability was determined for each time point using the same live/dead fluoromicroscopic staining assay as utilized in the study illustrated in FIG. 1.

In FIG. 3 the % viability was determined for porcine cartilage from intact osteochondral allografts that was stored either in standard culture media or in one of the PEG-containing compositions of the present invention. These data demonstrate that the supplementation of a standard cell growth medium, culture medium, or other physiologically and/or pharmaceutical formulation, with effective amounts of a biomembrane sealing agent such as PEG-600, PEG-3350, or a combination of two biomembrane sealing agents (i.e., PEG-600+PEG-3350) resulted in significantly-prolonged viability of the tissue during long-term storage.

These data indicated that the supplementation of standard cell growth medium with either low, or medium average MW PEG, or a combination of both PEGs, resulted in significant prolonging of tissue viability (compare FIG. 3 to the data of FIG. 2, same scale). While average culture medium alone retained approximately 90% viability at day 25; by day 35, no viable cells were identified. In contrast, the same medium supplemented with PEG-3350 along retained ~80% viability at least until day 36, while medium supplemented with PEG-600 retained ~85% viability for the same time interval. When the culture medium was supplemented with effective amounts of both lower and higher average MW polymers (in this case, PEG-600 and PEG-3350, respectively), tissue stored in the growth medium supplemented with the two PEGs remained ~90% viable at day 45, and retained at least 70% of its cellular viability at day 60—a time point that is several weeks after the viability of tissues stored in conventional formulations had decreased to undetectable levels.

In these studies, PEG-600 was employed at a working concentration of 1.3% (vol./vol.), PEG-3350 was employed at a working concentration of 1.5%-(wt./vol.), and the PEG-600+PEG-3350 combination (PEG-600/3350) was employed at a cumulative concentration of the two individual average MW PEG polymers (i.e., PEG-600 at 1.3% [vol./vol.]) and PEG-3350 at 1.5% [wt./vol.]). Tissues were maintained at refrigeration temperatures (~2° C. to 10° C.), and percent viability was determined using the same live/dead fluorescent microscopic assay as described in the previous studies supra.

The graphs depicted in FIG. 4 summarize the data presented in FIG. 2 and FIG. 3 by illustrating the percent viability of porcine cartilage from intact osteochondral allografts stored in PEG-supplemented standard culture medium at refrigeration temperature (~2° C. to about 10° C.) as determined using the live/dead fluoromicroscopic assay. These data clearly illustrate that significant improvement in viability was achieved by supplementing standard growth medium with one or more biomembrane sealing agents such as PEG, and a combination of two distinct PEGs (differing by their average MWs) provided particularly desirable results.

The data presented in FIG. 5 illustrate the additional beneficial effects that were observed when an antioxidant such as ascorbic acid was added to the PEG-supplemented standard growth medium. Here, these results are plotted in comparison to the average results of a number of standard culture media alone, lactated Ringer's solution alone, or a standard culture medium supplemented with two distinct biomembrane sealing agents (here PEG-600 and PEG-3350). These data demonstrate that the addition of the antioxidant significantly improved the performance of the storage medium compared to the other standard solutions.

FIG. 6 also shows enhancement of the viability prolonging properties of the storage solutions when a metal chelator such as deferoxamine mesylate or 2,2'-dipyridyl was added to the standard culture medium. The results were particularly significant for the first 30 days of storage (cf these results to those seen in FIG. 5).

Turning to FIG. 7, the percent viability of porcine cartilage from intact osteochondral allografts is again plotted as a function of storage time. This figure shows a combination of data from previous figures and illustrates base-line viability provided by lactated Ringer's solution, while also demonstrating the step-wise improvement in porcine cartilage viability obtained when standard culture medium was supplemented with (a) PEG-600/3350, (b) PEG-600/3350+ascorbic acid, and (c) PEG-600/3350+ascorbic acid+deferoxamine. Conditions and materials were the same as described in the legends to FIG. 1, FIG. 2, and FIG. 3.

The data shown in FIG. 8 is the same as presented in FIG. 7, but is illustrated with a change of scale to emphasize the significant short- to mid-term improvement in viability of provided by disclosed preservative compositions. Compare the results of (a) lactated Ringer's solution alone; (b) culture medium alone; (c) culture medium supplemented with PEG-600/3350 only; (d) culture medium supplemented with PEG-600/3350 and ascorbic acid; and (e) culture medium supplemented with PEG-600/3350, ascorbic acid, and the iron chelator, deferoxamine. Conditions and materials were the same as described in the legends to FIG. 1, FIG. 2, and FIG. 3.

The data in FIG. 9 illustrates the stark comparison between (a) lactated Ringer's solution alone; (b) culture medium alone; (c) culture medium+PEG-600/3350+ascorbic acid; and (d) culture medium+PEG-600/3350+ascorbic acid+deferoxamine. Conditions and materials were the same as described in the legends to FIG. 1, FIG. 2, and FIG. 3.

In each of the studies summarized in FIG. 1 through FIG. 9, and in Table 1 and Table 2 herein, 4-mm diameter biopsy punches were used to harvest samples of cartilage and bone for storage and subsequent staining. It was apparent from the staining that significant levels of cell death occurred at the biopsy edge due to the mechanical sampling of the cartilage and bone. Visual observation of those samples suggested that the addition of a biopolymer (e.g., PEG) alone, a biopolymer (e.g., PEG)+an antioxidant (e.g., ascorbic acid), or the tripartite supplementation of standard culture medium with a biopolymer (e.g., PEG) an antioxidant (e.g., ascorbic acid) and a chelator (e.g., deferoxamine) provided decreasing levels of edge death when compared to lactated Ringer's solution alone, or standard culture medium alone.

7. REFERENCES

The following references, to the extent that they provide exemplary procedural or other details supplementary to those set forth herein, are specifically incorporated herein by reference.

Baumert H, Simon P, Hekmati M, Fromont G, Levy M, Balaton A, Molinié V, Malavaud B, Campodonico F, and Schultheiss, "Development of a seeded scaffold in the great omentum: feasibility of an in vivo bioreactor for bladder tissue engineering," *Eur. Urol.*, December, 2006 (e-Pub ahead of print).

Campbell, G. R., and Campbell, J. H., "Development of tissue-engineered vascular grafts," *Curr. Pharm. Biotechnol.*, 8(1):43-50, 2007.

Good, N. E., et al., "Hydrogen ion buffers for biological research," *Biochemistry*, 5:467, 1966.

Huntley J S, Bush P G, McBimie J M, Simpson A H, Hall A C., "Chondrocyte death associated with human femoral osteochondral harvest as performed for mosaicplasty," *J. Bone Joint Surg. Am.*, 87(2):351-60, February, 2005).

MacNeil, S., "Progress and opportunities for tissue engineered skin," *Nature*, 445(7130):874-80, 2007.

Pennock A T, Wagner F, Robertson C M, Harwood Fla., Bugbee W D, Amiel D., "Prolonged storage of osteochondral allografts: does the addition of fetal bovine serum improve chondrocyte viability?" *J. Knee Surg.*, 19(4): 265-72, October, 2006.

Any of the compositions disclosed herein may be combined with any biologically-suitable formulation, pharmaceutical composition, growth medium, storage or transport buffer, or formulated in combination with one or more conventional tissue storage, transport or preservation solutions. Likewise, although only several exemplary embodiments have been described in detail herein, those skilled in the relevant arts will readily appreciate that many modifications are possible in the exemplary teachings without materially departing from the novel teachings and advantages of this disclosure. Accordingly, all such modifications and alternative are intended to be included within the scope of the invention as defined in the following claims. Those skilled in the art should also realize that such modifications and equivalent compositions, processes, or methods do not depart from the spirit and scope of the present disclosure, and that they may readily make various changes, substitutions, and/or alterations of the compositions herein without deviating from the spirit and scope of the present disclosure.

What is claimed is:

1. A composition comprising:
   a) a biological buffer, medium, tissue storage buffer or organ transport solution;
   b) a first polyethylene glycol and a second polyethylene glycol, the second polyethylene glycol having a different average molecular weight from the first polyethylene glycol;
   c) at least a first chelator selected from the group consisting of deferoxamine mesylate, 2,2'-dipyridyl, and 1,10-phenanthroline; and
   d) at least a first antioxidant selected from the group consisting of ascorbic acid and 2,6-di-tert-butyl-4-methylphenol;
   wherein each of b), c), and d) is present in said composition in an amount effective to prolong the viability of a biological sample maintained in said composition compared to maintenance of said biological sample stored in said biological buffer, medium, tissue storage buffer, or organ transport solution alone.

2. The composition of claim 1, wherein:
   a) the first polyethylene glycol is present in said composition at a concentration of between about 0.01% (vol./vol.) and about 30% (vol./vol);
   b) said at least a first chelator is present in said composition at a concentration of between about 0.01 μM and about 100 μM; or
   c) said at least a first antioxidant is present in said composition at a concentration of between about 0.0001% (vol./vol.) and about 0.30% (vol./vol.).

3. The composition of claim 1, further comprising at least a second distinct antioxidant, wherein said at least a first antioxidant is ascorbic acid, and
   said at least a second distinct antioxidant is 2,6-di-tert-butyl-4-methylphenol.

4. A method for storing a biological sample, comprising:
   a) contacting a biological sample with a composition according to claim 1;
   and
   b) maintaining said sample in said composition at a temperature of from between about −10° C. and about 25° C.,
   wherein said biological sample remains substantially viable after maintaining said sample in said composition for a period of at least about 14 days.

5. The method of claim 4, wherein said biological sample comprises a population of mammalian cells, a mammalian tissue, a mammalian organ, a tissue engineered construct or a tissue engineered device.

6. The method of claim 5, wherein at least about 70% of said biological sample remains substantially viable after maintaining said sample in said composition for a period of at least about 21 days.

7. The method of claim 6, wherein at least about 70% of said biological sample remains substantially viable after maintaining said sample in said composition for a period of at least about 42 days.

8. The method of claim 7, wherein at least about 50% of said biological sample remains substantially viable after maintaining said sample in said composition for a period of at least about 58 days.

9. The method of claim 4, wherein the first polyethylene glycol is present in said composition at a concentration of between about 0.10% (vol./vol.) and about 10% (vol./vol.).

10. The method of claim 4, wherein said mixture comprises at least a first polyethylene glycol having an average molecular weight of about 600 Da, and at least a second polyethylene glycol having an average molecular weight of about 3350 Da.

11. The method of claim 10, wherein each of said first and said second polyethylene glycols is present in said composition at a concentration of from between about 0.1% and 5% (vol./vol.).

12. The method of claim 11, wherein each of said first and said second polyethylene glycols is present in said composition at a concentration of about 1.3%.

13. The method of claim 4, wherein said at least a first chelator is present in said composition at a concentration of between about 0.01 µM and about 20 µM.

14. The method of claim 4, wherein said compound is deferoxamine mesylate.

15. The method of claim 4, wherein said at least a first antioxidant is present in said composition at a concentration of between about 0.010% (vol./vol.) and about 1.0% (vol./vol.).

* * * * *